Figure 2:
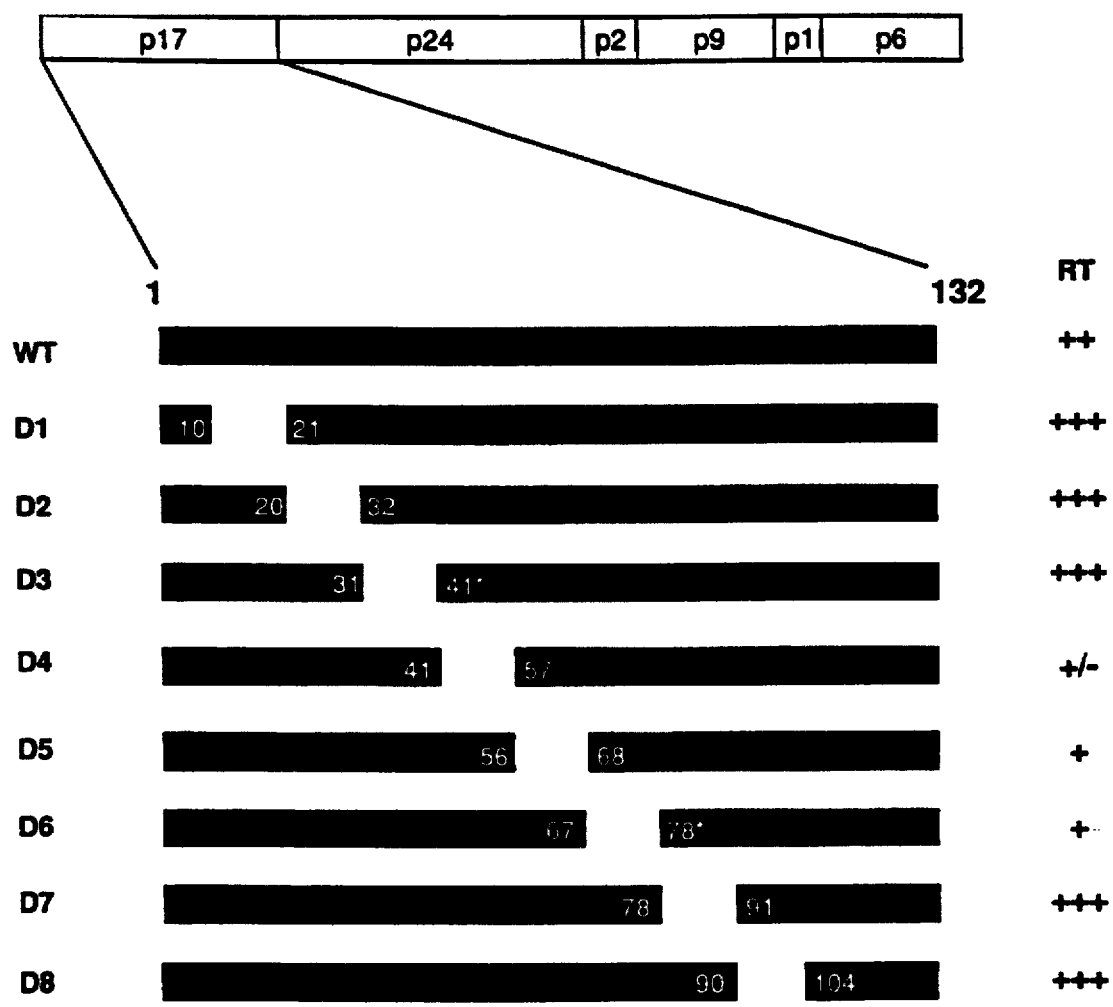

US005707864A

United States Patent [19]

Essex et al.

[11] Patent Number: 5,707,864
[45] Date of Patent: Jan. 13, 1998

[54] NUCLEIC ACIDS ENCODING MUTATED HUMAN IMMUNODEFICIENCY VIRUS MATRIX PROTEINS

[75] Inventors: Myron E. Essex, Sharon, Mass.; Xiaofang Yu, Columbia, Md.; Tun-Hou Lee, Newton, Mass.

[73] Assignee: President and Fellows of Harvard College, Cambridge, Mass.

[21] Appl. No.: 979,966

[22] Filed: Nov. 23, 1992

[51] Int. Cl.$^6$ .............................. C12N 15/49; C12N 5/10; C12N 15/63; C07K 14/155

[52] U.S. Cl. .................. 435/325; 435/320.1; 536/23.72; 514/44; 424/93.1; 424/93.2; 424/93.21; 930/221

[58] Field of Search ........................... 514/44; 424/93.1, 424/93.2, 93.21; 435/325, 320.1; 536/23.72

[56] References Cited

PUBLICATIONS

Yu et al., "Functional Study of HIV-1 Matrix proteins in virus assembly an infectivity", *International Conference on AIDS (Netherlands)*; 8:0003, See Abstract No. 0003; No. 1, issued 19–24 Jul. 1992.

Yu et al, "The C Terminus of Human Immunodeficiency Virus Type 1 Matrix Protein Is Involved in Early Steps of the Virus Life Cycle", *Journal of Virology*, 66:5667–5670, Sep., 1992, Yu, X., et al., "The Matrix Protein of Human Immunodeficiency Virus Type 1 Is Required for Incorporation of Viral Envelope Protein into Mature Virions", 1992, J. Virology, 66(8):4966–71.

Natsoulis and Boeke, New Antiviral Strategy using Capsid–nuclease Fusion Proteins, Nature 352:632–635, 1991.

Pal et al., Myristoylation of gag Proteins of HIV–1 Plays an Important Role in Virus Assembly, AIDS Research and Human Retroviruses 6:721–730, 1990.

Rhee and Hunter, Structural Role of the Matrix Protein of Type D Retroviruses in Gag Polyprotein Stability and Capsid Assembly, J. Virology 64:4383–4389, 1990.

Rhee and Hunter, Amino Acid Substitutions within the Matrix Protein of Type D Retroviruses Affect Assembly, Transport and Membrane Association of a Capsid, EMBO Journal 10:535–546, 1991.

Smith et al., Human Immunodefiency Virus Type I Pr55gag–pol Expressed from a Simian Virus 40 Late Replacement Vector . . . Assembled into Viruslike Particles, J. Virology 64:2743–2750, 1990.

Trono et al., HIV–1 Gag Mutants can Dominantly Interfere with the Replication of the Wild–Type Virus, Cell 59:113–120, 1989.

Pozansky et al., J. Virol. 65:532, 1991.

Kotin et al., PNAS 87:2211, 1990.

Chatterjee et al., Science 258:1485, 1992.

Curiel et al., PNAS 88:8850, 1991.

Curiel et al., Hum. Gene Ther. 3:147, 1992.

Wolff et al., Science 247:1465, 1990.

Wang et al., PNAS 90:4156, 1993.

"Report and Recommendations of the Panel to Assess the NIH Investment in Research on Gene Therapy," Orkin and Motulsky, Co–chairs, Dec. 7, 1995.

M. I. Johnston et al. (1993) Science 260:1286–1293.

D. Cournoyer et al. (1993) Annu. Rev. Immunol. 11:297–329.

M. B. Feinberg et al. (1992) AIDS Research and Human Retroviruses 8(6):1013–1022.

S.–J. Lee et al. (1989) AIDS Research and Human Retroviruses 5(4): 441–449.

H. Shimizu et al. (1992) Virology 189:534–546.

J.A.T. Young et al (1990) Science 250:1421–1423.

L. A. Lasky et al. (1987) Cell 50:975–985.

*Primary Examiner*—George G. Elliott
*Assistant Examiner*—Johnny F. Railey, II
*Attorney, Agent, or Firm*—Fish & Richardson P.C.

[57] ABSTRACT

Nucleic acid constructs encoding mutated human immunodeficiency virus matrix proteins are described. The mutated proteins lower the incorporation of envelope polypeptides in viral particles, disrupt viral assembly or disrupt viral entry into uninfected cells.

24 Claims, 18 Drawing Sheets

FIG. 3A
FIG. 3B
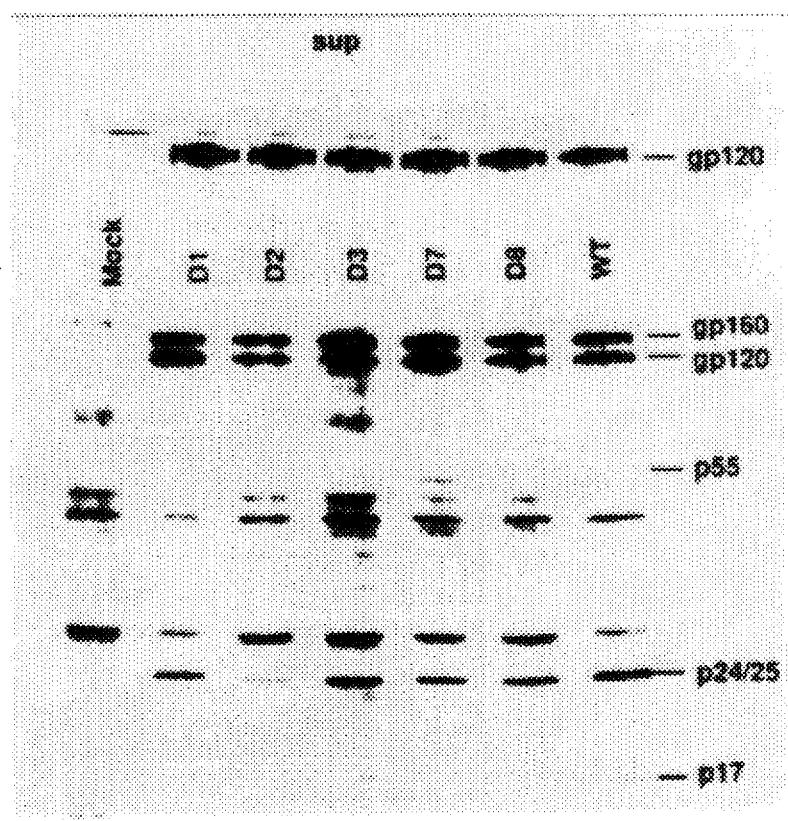
FIG. 3C
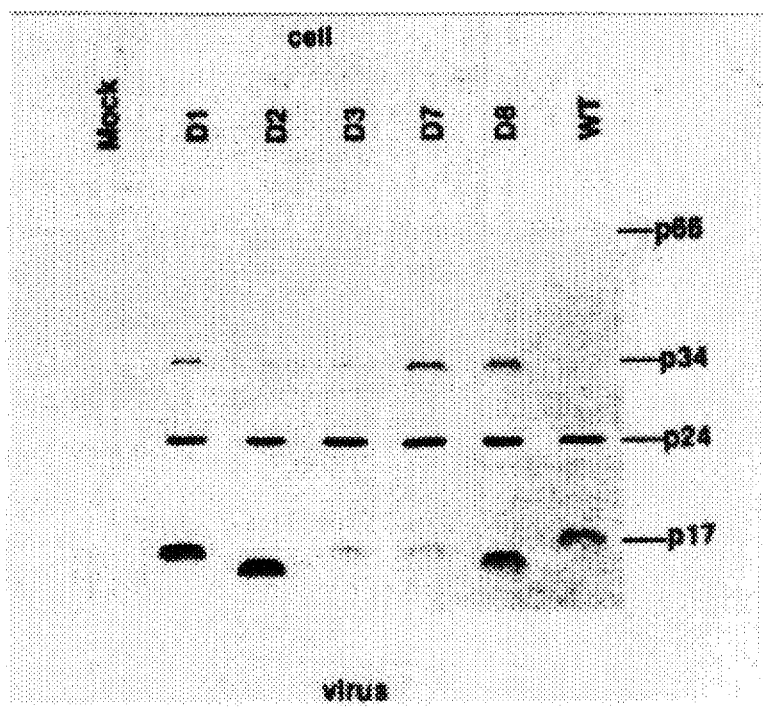

DAYS AFTER INFECTION

HIV-1 *gag*

```
               104                                    132
WT    IEEEQNKSKKKAQQAAADTGHSNQVSQNY
D9    L----------AQQAAADTGHSNQVSQNY
D10   IEEEQNKSKKKA---------------SQNY
```

| | | |
|---|---|---|
| HIV-1(HXB2R3) p17 | AADTGHSNQV | aa 119-128 |
| Coxsackie B1 VP1 | AAETGHTsQV | aa 603-612 |
| Rhinovirus 1B VP1 | AAETGHTsNV | aa 606-615 |
| Poliovirus VP1 | AvETGaTNpL | aa 624-633 |
| Dengue 2J E | iAETqHgtiV | aa 592-601 |

NUCLEIC ACIDS ENCODING MUTATED HUMAN IMMUNODEFICIENCY VIRUS MATRIX PROTEINS

STATEMENT AS TO FEDERALLY SPONSORED RESEARCH

This invention was funded at least in part by the United States government and the government has certain rights in the invention.

BACKGROUND OF THE INVENTION

This invention relates to the treatment of infection with the human immunodeficiency virus (HIV) by which we mean to include all of the various viral types and strains denominated by that term, such as HTLV-III, LAV, ARV, HIV-1, HIV-2, and LAV-2.

HIV is an etiological agent of Acquired Immune Deficiency Syndrome (AIDS). An example of HIV (now denominated HIV-1) is generally described in several articles: Barre-Sinoussi et al., Science 220:868, 1983; Gallo et al., Science 224:500, 1984; Popovic et al., Science 224:497, 1984; and Levy et al., Science 225:840, 1984, each of which is hereby incorporated by reference. Various isolates of HIV-1 have been obtained from North America, Western Europe and Central Africa. These isolates differ somewhat in their nucleotide sequence, but the proteins they encode are generally antigenically cross-reactive.

A second virus related to HIV-1 has been isolated and termed HIV-2. This virus is reported by Guyader et al., Nature 326:662, 1987; Brun-Vezinet et al., The Lancet 1:128, 1987; and Clavel et al., Science 233:343, 1986, each of which is hereby incorporated by reference. The genetic organization of HIV-2 is similar to that of HIV-1.

A group of viruses isolated from monkeys, termed simian immunodeficiency virus (SIV or STLV-III), is related to HIV-1 and HIV-2, particularly the latter. See Daniel et al., Science 228:1201–1204 (1985); Kanki et al., Science 230:951–954 (1985); Chakrabarti et al., Nature 328:543–547 (1987); and Ohta et al., Int'l. J. Cancer 41:115–222 (1988), each of which is hereby incorporated by reference. Members of this viral group exhibit minor variations in their genomic sequences, and have some differences in their restriction enzyme maps.

Assembly of retroviruses requires the correct folding and intracellular transport of the Gag polyprotein, association of the Gag polyprotein with the cellular membrane, and ultimately the release of assembled virions from the plasma membranes of infected cells. A portion of the Gag polyprotein having a molecular weight of about 17 Daltons is known as the matrix (MA) protein. MA plays an important role in all of the above aspects of viral assembly and release. In most retroviruses, the MA protein is modified by the addition of myristic acid at the N-terminal glycine residue (Schultz et al., Annu. Rev. Cell Biol. 4:611–647, 1988). In addition to their role in myristoylation, sequences within the MA protein are important for Gag polyprotein transport and virus assembly (Hansen et al., J. Virol. 64:5306–5316, 1990; Wills et al., J. Virol. 65:3804–3812, 1991).

HIV has already entered large segments of the world population, and substantial effort has been directed toward developing treatments for individuals infected with it. In addition to investigation of synthetic pharmaceuticals, effort has been directed toward utilizing variants of HIV-1 and HIV-2 to design AIDS therapeutics.

Deletions or point mutations within the MA protein of Mason-Pfizer monkey virus (MPMV) affected the stability of Gag polyprotein and virus assembly (Rhee and Hunter, J. Virol. 64:4383–4389, 1990; Rhee and Hunter, EMBO J. 10:535–546, 1990). Point mutations also blocked the transport of preassembled MPMV capsids to the plasma membrane and blocked the release of virions from the cell surface (Rhee and Hunter, EMBO J. 10:535–546, 1990). An amino acid substitution in the MA protein of MPMV converted a type D retrovirus to a type C retrovirus (Rhee and Hunter, Cell 63:77–86, 1990).

Trono et al. (Cell 59:113–120, 1989), state that certain mutations in the DNA encoding the p24 and p15 polypeptides disrupt viral replication.

SUMMARY OF THE INVENTION

The invention features a method of treating a patient infected with human immunodeficiency virus (HIV) by administering to the patient a mutated HIV matrix (MA) polypeptide in an amount effective to reduce effective HIV levels in the patient. Also a part of the invention are methods of treating a patient by the administration of a therapeutic composition composed of the mutated MA polypeptide in a pharmaceutically acceptable carrier.

Also included in the invention is a method of treating a patient infected with HIV by administration of a nucleic acid encoding the mutated MA polypeptide in an expressible genetic construction. Preferably, the expressible genetic construction is capable of remaining stably in cells of the patient and thereby transforming the cells of the patient.

Such an expressible genetic construction may be a viral vector capable of infecting said patient. The nucleic acid sequence may also include a sequence encoding a CD4-binding polypeptide, or a nucleic acid sequence encoding a gp120-binding polypeptide, or fragments thereof.

The invention further includes a method of treating an HIV infected patient by removing cells from the patient, transforming the cells with the nucleic acid as described above, and returning transformed cells to the patient's body.

The invention also provides a method of therapy whereby the genetic construction is administered directly to the patient. The viral vector used for any of the methods of nucleic acid administration may be human immunodeficiency virus-type I.

The invention also provides a method for treating a patient infected with HIV wherein the mutated MA polypeptide contains a deletion or substitution of at least one amino acid in at least one of the following regions of a wild type MA polypeptide:

amino acids 5–16 of said wild-type;
amino acids 11–20 of said wild-type;
amino acids 21–31 of said wild-type;
amino acids 32–43 of said wild-type;
amino acids 57–67 of said wild-type;
amino acids 66–77 of said wild-type;
amino acids 79–90 of said wild-type;
amino acids 91–103 of said wild-type;
amino acids 105–114 of said wild-type;
amino acids 116–128 of said wild-type;
substitution of Arg36 and Pro37 for Trp36 and Ala37;
substitution of Thr20 for Arg20 and Asn18, 26, 27, 28, 30 and 32 for Glu18, 26, 27, 28, 30 and 32; or
a substitution of Thr20 for Arg20 and Asn18, 26, 27, 28, 30, and 32 for Lys18, 26, 27, 28, 30 and 32 the deletion or substitution being effective for at least one of the following:

(a) lowering the incorporation of Env polypeptides in the viral particle in HIV infected cells;
(b) disrupting viral assembly in HIV infected cells; or
(c) disrupt viral entry into uninfected cells.

Also a part of the invention is a therapeutic composition adapted for administration to a patient infected with human immunodeficiency virus-type I (HIV-1), including a mutated MA polypeptide in a pharmaceutically acceptable carrier or a nucleic acid encoding a mutated MA polypeptide in an expressible genetic construction, preferably for transforming cells of a human patient. The nucleic acid which is administered to the patient may be a part of a viral vector capable of infecting the patent and/or the nucleic acid may contain a sequence capable of encoding a CD4-binding polypeptide, a gp120-binding polypeptide, or a fragment thereof.

By a mutated MA is meant an MA polypeptide having a deletion, insertion, substitution or other modification rendering the MA polypeptide effective as an inhibitor of pathogenic HIV viral replication, assembly, or infectivity by one of the assays described below.

Particularly useful are the transfection, infection, and RT assay and radioimmunoprecipitation, immunoblot, and pulse chase assay procedures. Specifically, useful to identify mutations which disrupt ENV protein incorporation are viral mutations which result in normal levels of the gag and pol proteins, but confer decreased levels of the gp120 and gp41 proteins in the virion. Mutations which affect infectivity may be identified by the infectivity assay. Useful mutations affecting infectivity are those mutations which decrease infectivity by 20%, preferably 40% and most 80% or more. Mutations which affect viral replication and therefore have the therapeutic promise are those which decrease viral replication relative to wild-type virus, preferably decreasing replication by 10% and most preferably decreasing replication by 20% or more in a co-transfection assay.

The mutated MA polypeptides included in the invention may be the equivalent mutation MA proteins from other strains of HIV. One skilled in the art may determine the equivalent mutations based upon amino acid and nucleic acid homology even if the exact residue number is not the same.

Preferably the mutations according to the invention do not affect expression of the gag precursor, nor do they block processing of the precursor to yield component gag proteins. Also, preferably, the mutated MA proteins retain the ability to interact with their wild-type gag counterparts, thereby improving the transdominant negative function of the mutants.

Other features and advantages of the invention will be apparent from the following description of the preferred embodiments of the invention and from the claims.

DESCRIPTION OF THE PREFERRED EMBODIMENTS

The drawings will first be briefly described. Drawings FIG. 1 is the sequence of the nucleic acid encoding the MA polypeptide and the amino acid sequence of the MA polypeptide (SEQ ID NO:1) (SEQ ID NO:2).

FIG. 2 depicts the construction and virus production of MA mutants D1 to D8. Results of reverse transcriptase (RT) assay symbols:±, 10,100 to 40,000 cpm/ml; +, 50,000 to 100,000 cpm/ml; ++, 150,000 to 350,000 cpm/ml; +++500, 000 to 950 cpm/ml.

FIGS. 3A–D depicts detection of viral proteins. Detection of viral proteins in transfected COS-7 cells, supernatants, and virus pellets by RIPA (a, b, and c) and pulse-chase labeling (d).

FIG. 4 is a graph of virus infectivity of D1–D8 mutants of MA.

FIGS. 5A–B (A) depicts analysis of D1–D8 viral proteins by immunoblot. (B) depicts analysis of R3WA and R3AP viral proteins by immunoblot.

FIG. 6 is a graph of the dominant negative mutant assay for the D1 and D2 mutants.

FIGS. 7A–C depicts (a) construction of the D9 and D10 mutants (b) sequence homology among HIV-1 MA and other viruses and (c) virus infectivity (SEQ ID NO: 3) (SEQ ID NO: 4) (SEQ ID NO: 5) (SEQ ID NO: 6) (SEQ ID NO: 7( SEQ ID NO: 8) (SEQ ID NO: 9) (SEQ ID NO: 10).

FIGS. 8A–C depicts analysis of viral proteins and virion-associated RNA. (A) Viral proteins from transfected COS-7 cells were analyzed by radioimmunoprecipitation as previously described (29). (B) Viral proteins from purified virions analyzed by immunoblot with a sheep anti-gp 120 serum (top) and pooled HIV-1-positive human sera (bottom). (C) Viral RNA analyzed by dot blot assay.

FIG. 9 is analysis of D9 and D10 DNA synthesis after infection.

FIG. 10 is a graph of dominant negative mutant assay for D9 and D10.

FIGS. 11A–B depicts analysis of D0, B5, and B8 viral proteins by immunoblot.

FIG. 12 is a graph of dominant negative mutant assay for D0.

FIG. 13 depicts a viral construct with the nucleic acid encoding MA in an expressible position.

I. MA Polypeptides

Without wishing to bind ourselves to specific modes of action, it appears that there are at least three classes of MA polypeptides which are useful as therapeutics for HIV infection.

The first class of MA polypeptides which are therapeutically useful are those which disrupt the incorporation of the Env polypeptides gp120 and gp41 into the viral particle in a dominant negative manner. Such MA mutants result in the production of non-infectious particles which incorporate the viral proteins synthesized by the pathogenic HIV. Mutants useful for this purpose may be identified by first testing candidate alterations for detectable levels of synthesis and stability of both Gag and Env polyproteins, this may be done by the methods provided below in Section IV and in the examples. By detectable levels synthesis and stability is meant that levels of synthesis and stability are, taken together, at least 15% of that which is detected with wild-type virus. Secondly, useful MA polypeptides of this class are further distinguished by their ability to disrupt pathogenic HIV replication in a trans-dominant manner using the dominant negative mutant assay described below. MA polypeptides with therapeutic promise will have activity in the dominant negative assay which is at least five-fold lower than wild-type between days 1 and 10 of the assay. The desirable mutant is correctly synthesized and localized, but blocks stable incorporation of the Env proteins encoded by the pathogenic virus, thereby resulting a failure of the cell to yield infectious particles.

MA polypeptides with the useful therapeutic characteristic of disrupting functional Env protein incorporation include those MA polypeptides with deletions, insertions, or point mutations between amino acids 3 and 104. Preferred mutations of this class include the MA mutations D1 (a deletion between amino acids 10 and 21), D2 (deletion between amino acids 20 and 32), D3 (deletion between 31 and 41), D7 (deletion between 78 and 91) and D8 (deletion between 90 and 104) and point mutations (for example 1) the change of Trp36 and Ala37 to Arg and Pro (R3WA), respectively, and 2) the change of Ala 37 to Pro (R3AP)).

A second class of MA mutants useful for the therapeutic treatment of HIV infection are those MA alterations which, when incorporated into the viral particle, disrupt entry of this virus into uninfected cells. This phenotype may be identified using tests of viral infectivity provided in the examples. In addition to this characteristic, desirable mutations should synthesized and localized at normal levels, as indicated above. Such mutations may be further identified using the dominant negative assay described below and selecting those mutations which confer a five-fold or greater reduction in RT Values relative to wild-type between days 1 and 10 of the assay.

Those skilled in the art will appreciate that other MA mutations (including deletions, substitutions or additions to naturally occurring (wild type) MA sequences can be used according to the invention. Techniques for generating a universe of candidate mutants are well known to those in the art. One such technique features random mutagenesis as described by Rhee and Hunter (EMBO, 10:535–546, 1990). The pool of candidate mutants can then be screened for their ability to disrupt incorporation by various techniques including the techniques described in Examples 1 to 3, below.

Mutations useful for anti-HIV therapy by virtue of their disruption of virus entry include, but are not limited to, mutations which alter the region between amino acids 104 and 132 (see D9 and D10, FIG. 7).

A third class of MA mutants useful for anti-HIV therapy are those mutations which disrupt the assembly and/or release of virions. These mutations may be identified by screening for normal synthesis and stability of Gag polyproteins and a failure to assemble virions and a positive result indicating inhibitory effect in the dominant negative mutant assay, by the criterion indicated above. An example of a MA mutant with the characteristics which are desirable is described in Example 3. This example is a deletion of amino acids 5 to 16 of the MA polypeptide.

II A. Therapeutic Administration of MA Polypeptide.

As described in greater detail in the examples below, MA mutants according to the invention are effective HIV therapeutics because they function in a so-called "transdominant" fashion. Specifically, it appears that the MA mutants become physically associated with an otherwise pathogenic virion component being manufactured in an HIV-infected cells. As a result, the load of properly assembled infectious virions that cell manufactures is reduced in proportion to the mutant MA levels in the cell. When mutant MA is delivered to the cell in sufficient excess, the incidence of ineffective viral assembly resulting from attempts to incorporate mutant MA becomes far higher than the incidence of incorporation of wild type MA.

With the availability of the cloned gag gene (Bryant et al., Proc. Natl. Acad. Sci., 87:523, 1990; Göttlinger et al. Proc. Natl. Acad Sci., 86:5781, 1989; Gowda et al., Journal of Virology, 63:1451, March 1989; Mervis et al., Journal of Virology, 62:3993, November 1988; Kramer et al., Science, 231:1580, March 1986; Smith et al., Journal of Virology, 64:2743, June 1990) the substantially pure MA polypeptide can be produced in quantity using standard techniques (Scopes, R. *Protein Purification: Principles and Practice*, Springer-Verlag, N.Y. 1982). Thus, another aspect of the invention is a pharmaceutical comprising the MA polypeptide together with an acceptable diluent, carrier or excipient and/or in unit dosage form. Conventional pharmaceutical practice may be employed to provide suitable formulations or compositions to administer the polypeptide to patients infected with HIV.

A substantially pure preparation of a polypeptide is a preparation which is substantially free (e.g., to the extent required for formulating MA into a therapeutic composition) of the proteins with which it naturally occurs in a cell.

Fragments or analogs of the MA protein may also be administered to a patient infected with HIV in the manner described above. Fragments or analogs which are useful for this purpose include fragments and analogs of peptides described herein which are useful for the treatment of a patient infected with HIV-1. Fragments and analogs which will be useful for the therapeutic treatment of patients infected with HIV-1 are determined using the assays provided in the examples, below, among others.

The MA polypeptide may also be administered to a patient infected with HIV in the form of a fusion protein consisting of a mutated MA polypeptide, fused to the gp120 protein, or a fragment thereof which is sufficient to bind the CD4 receptor of T cells, monocytes, macrophages or other cell types infected by HIV. This fusion protein allows delivery of the desirable MA polypeptide into uninfected T cells, monocytes, macrophages or other cell types infected by HIV and expressing the CD4 receptor.

The mutated MA polypeptide may also be administered to a patient infected with HIV in the form of a fusion protein consisting of the desirable MA polypeptide, or a therapeutically useful fragment or derivative, fused to the CD4 protein, or a fragment thereof, which is sufficient to bind gp120. This fusion protein allows delivery of the desirable MA polypeptide into infected T cells expressing gp120 on their surface. The MA-gp120 fusion polypeptide or the MA-CD4 fusion polypeptide may be generated using standard techniques of molecular biology to generate fusions encoded from a suitable vector (Sambrook et al., *Molecular Cloning: A Laboratory Manual*, Cold Spring Harbor Laboratory Press, N.Y. (1989)). Either the gp120 fragment or the CD4 fragment may enable internalization of the MA polypeptide through endocytosis. The sequences of both the gp120 and CD4 genes for the stated use may be obtained from Maddon et al., *Cell* 42:93, August, 1985; Weaver et al., *Cell*, 45:247, 1986; Rekosh et al, Proc. Natl. Acad. Sci., 85:334, 1988; Chanda et al., Vaccines, :207, 1989 and Hammarskjold et al., Journal of Virology, 63:1959, 1989. The usefulness of such gene fusions constructs may be determined using the methods described below in the examples, among others. The invention includes administering either fusion polypeptide alone in a pharmaceutically acceptable carrier, or administering both fusions together in an acceptable carrier.

Thus, the formulations of this invention can be applied for example by parenteral administration, intravenous, subcutaneus, intramuscular, intracranial, intraorbital, opthalmic, intraventricular, intracapsular, intraspinal, intracisternal, intraperitoneal, intranasal, aerosol, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences". Formulations for parenteral administration may, for example, contain excipients sterile water or saline, polyalkylene glycols such as polyethylene glycol, oils of vegetable origin, or hydrogenated napthalenes. Biocompatible, biodegradable lactide polymer, lactide/ glycoside copolymer, or polyoxyethylenepolyoxypropylene copolymers may be used to control the release of present factors. Other potentially useful parenteral delivery systems for the factors include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

II B. Construction of HIV Containing encoding the mutated MA polypeptide

A particularly preferred embodiment features administering to the patient genetic constructions which encode any of the MA polypeptides described herein, and (after transformation of patient cells) can express the MA polypeptide.

In addition to the HIV example below illustrating a preferred viral vehicle, those skilled in the art will readily appreciate that the invention can use other HIV-1 or HIV-2 strains of the many that have been fully characterized e.g., MN, HXB2, LAI, NL43, MFA, BRVA and z321.

Moreover, there are numerous other viral vehicles (i.e., nucleic acid vehicles which can activate or be activated to enter cells of the host organism and, having done so, to be expressed there.

II C. Therapeutic Administration of MA in a Viral Vector.

Retroviral vectors, or other viral vectors with the appropriate tropisms for cells infected by HIV, may be used as a gene transfer delivery system for the MA polypeptide. Numerous vectors useful for this purpose are generally known have been described (Miller, Human Gene Therapy 15–14 (1990); Friedman, Science 244:1275–1281 (1989); Eglitis and Anderson, BioTechniques 6:608–614 (1988); Tolstoshev and Anderson, Current Opinion in Biotechnology 1:55–61 (1990); Sharp, The Lancet 337:1277–1278 (1991); Cornetta et al., Nucleic Acid Research and Molecular Biology 36:311–322 (1987); Anderson, Science 226:401–409 (1984); Moen, Blood Cells 17:407–416 (1991); and Miller and Rosman, Biotechniques 7:980–990 (1989)). Retroviral vectors are particularly well developed and have been used in a clinical setting (Rosenberg, et al N. Engl. J. Med 323:370 (1990)).

The retroviral constructs, packaging cell lines and delivery systems which may be useful for this purpose include, but are not limited to, one, or a combination of, the following: Moloney murine leukemia viral vector types; self inactivating vectors; double copy vectors; selection marker vectors; and suicide mechanism vectors. The Moloney murine leukemia retroviral system of MA delivery is particularly useful since it targets delivery of the MA protein to the hematopoietic cells which ultimately give rise to the T-cells. The delivery of the MA polypeptide can be further restricted to cells which are infected by HIV-1 directly by virtue of utilizing retroviral constructs in which the HIV-LTR is used to drive expression from the gag gene. To achieve proper expression from such a construct the 3'LTR of the Moloney murine leukemia vector must be deleted. Vector strategies which include either the entire HXB2UX construct or the gag gene driven by the HIV-LTR are shown in FIG. 13.

Fragments or derivatives of the MA polypeptide may also be administered by retroviral gene transfer therapy or another suitable viral vector system. Fragments or derivatives are defined as described above. Useful fragments or derivatives of MA may be administered by inserting the nucleic acids encoding these fragments or derivatives in place of the complete gag gene in a gene therapy vector, as described above. Such constructs may be tested using the methods for testing the effects of MA on viral infectivity described above, among others.

Retroviral delivery of MA is particularly appropriate in HIV-1 infected individuals who display the common secondary appearance of B-cell tumors as a result of immunodeficiency. These individuals may undergo bone marrow removal, treatment, and reimplantation as a matter of course for the treatment of the B-cell tumors. At this time standard techniques for the delivery of gene therapy vectors may be used to transfect stem cells. Such transfection may result in MA synthesizing T-cells useful in lowering the infective levels of HIV-1 in the patient.

II D. Non viral methods for the therapeutic delivery nucleic acid encoding MA

Nucleic acid encoding MA, or a fragment thereof, under the regulation of the HIV-LTR and including the appropriate sequences required for insertion into genomic DNA of the patient, or autonomous replication, may be administered to the patient using the following gene transfer techniques: microinjection (Wolff et al., Science 247:1465 (1990)); calcium phosphate transfer (Graham and Van der Eb, Virology 52:456 (1973); Wigler et al., Cell 14:725 (1978); Felgner et al., Proc. Natl. Acad. Sci. USA 84:7413 (1987)); lipofection (Felgner et al., Proc. Natl. Acad. Sci. USA 84:7413 (1987); Ono et al., Neuroscience Lett 117:259 (1990); Brigham et al., Am. J. Med. Sci. 298:278 (1989); Staubinger and Papahadjopoulos, Meth. Enz. 101:512 (1983)); asialorosonucoid-polylysine conjugation (Wu and Wu, J. Biol. Chem. 263:14621 (1988); Wu et al., J. Biol. Chem. 264:16985 (1989)); and electroporation (Neumann et al., EMBO J. 7:841 (1980)). These references are hereby incorporated by reference.

V. Mode of MA Action

Without wishing to bind ourselves to a specific explanation for the mode of action of the invention, the results disclosed herein indicate that the HIV MA protein plays an important role in early steps of the virus life cycle. Although the MA protein's involvement in the process of reverse transcription cannot be excluded, studies using transmission electron microscopy suggests that the entry of the mutant virus cell into the host might be affected.

The possible role of murine leukemia virus Gag proteins in the early stages of virus infection has been previously reported (Crawford and Goff, J. Virol. 49:909–917, 1984). Deletions in murine leukemia virus Gag protein p12, or p12 and p15 (MA) together, have been shown to block viral replication at steps prior to reverse transcription. However, it is not clear whether p12 or the MA protein or both were responsible for the observed phenomenon, as the cleavage between the MA protein and p12 was affected in all of the mutants (Crawford and Goff, J Virol. 49:909–917, 1984).

III. METHODS

DNA, cells, and sera. The molecular clone of HIV-1, HXB2R3, was constructed by exchanging the XhoI-XbaI fragment from HXB2R (Yun et al., AIDS Res. Hum. Retroviruses 6:1265–1271, 1990) with the XhoI-XbaI fragment from HXB3 (Ratner et al., AIDS Res. Hum. Retroviruses 3:57–69, 1987). This fragment includes the 3' long terminal repeat and part of the nef coding sequence. In contrast to HXB2 (Ratner et al., AIDS Res. Hum. Retroviruses 3:57–69, 1987), HXB2R3 contains full-length vpr and new coding sequences. COS-7 cells were maintained in Dulbecco's modified Eagle's medium plus 10% fetal calf serum. SupT1 cells were maintained in RPMI 1640 medium plus 10% fetal calf serum. HIV-1-positive human sera were kindly provided by K. Meyer of the Fenway Community Health Center, Boston, Mass. The sheep anti-gp120 serum of HIV-1 was obtained from the AIDs Research and Reference Program (catalog no. 192), National Institutes of Health, Bethesda, Md.

Oligonucleotide-directed mutagenesis of MA. The SstI-ApaI fragment covering the gag region of HXB2R3 was subcloned into pGEM7Z(+) (Promega, Madison, Wis.). Single-stranded uracil-containing DNA was prepared and used for site-directed mutagenesis according to the protocol of the manufacturer (Bio-Rad, Richmond, Calif.). The sequences of primers used for mutagenesis were as follows: D1, 5'-CCC CCT GGC CTT AAC CCG CTT AAT ACT G-3' (SEQ ID NO:11); D2, 5'-CCA TAC TAT ATG TTT TCG AAT TTT TTC CCA TCG-3' (SEQ ID NO:12); D3, 5'-AAC TGC GAA TCG TTC TAT TAA TTT ATA TTT TTC-3' (SEQ ID NO:13); D4, 5' CAG TAT TTG TCT ACA GAG CTC CCT GCT TGC CC-3' (SEQ ID NO:14); D5, 5'-TGA TCC TGT CTG AAG GCC TTC TGA TGT TTC-3' (SEQ ID NO:15); D6, 5'-TAC TGT ATT ATA TAT CGA TGG TTG TAG CTG TCC-3' (SEQ ID NO:16); D7, 5F-CTT TTA TCT CTA TTC TAG ATC TAA GTT CTT C-3' (SEQ ID NO:17); D8, 5'-TTG CTC TTC CTC TAT TTG ATG CAC ACA ATA G-3' (SEQ ID NO:18); Myr⁻, 5'-TGA CGC TCT CGC GAC CAT CTC TCT CC-3' (SEQ ID NO:19). The positions of MA deletion mutants are illustrated in FIG. 1. The myristoylation mutant, Myr⁻, contains a substitution of valine for glycine at amino acid position 2. Mutants were screened by restriction enzyme digestion and DNA sequencing. The BssHII-PstI fragments which contain the MA mutations were cloned back into the vector of HXB2R3.

Transfection, infection, and RT assay. COS-7 cells were trypsinized and seeded at about 30% confluence 24 h before transfection. Cells (5×10⁶) were then trypsinized pelleted, and resuspended in 1 ml of TD buffer (25 mM Tris-HCL, ph 7.4; 140 mM NaCl; 5 mM Kcl; 0.7 mM K₂HPO₄) containing 400 µg of DEAE-dextran and 2 µg of wild-type or mutant DNA. Transfection was carried out at 37° C. for 30 min. For the transfection of SupT1 cells, the trypsinization step was omitted. SupT1 cells (10⁷) were washed once with phosphate-buffered saline and resuspended in 3 ml of TD buffer containing 600 µg of DEAE-dextran and 6 µg of DNA. The DNAs used for each SupT1 transfection were as follows: mock, 6 µg of pUC18; wild-type, 1 µg of HXB2R3 plus 5 µg of PUC18; wild-type+D1, 1 µg of HXB2R3 plus 5 µg of D1; wild-type+D2, 1 µg of HXB2R3 plus 5 µg of D2; wild-type+Myr⁻, 1 µg of HXB2R3 plus 5 µg of Myr⁻. Transfections were carried out at room temperature for 20 min. Virus infectivity was tested with SupT1 cells by using cell-free supernatants of transfected COS-7 cells as previously described (Yu et al., J. Virol. 64:5688–5693, 1990). Samples used in the reverse transcriptase (RT) assay were prepared from polyethylene glycol-precipitated viral pellets from the supernatant of transfected or infected cells. The assay was performed as previously described (Yu et al., J. Virol. 64:5688–5693, 1990).

Radioimmunoprecipitation, immunoblot, and pulse-chase analysis. At 60 h posttransfection, COS-7 cells were incubated for 12 h in cystsine-free RPMI 1640 medium containing [³⁵S]cysteine (0.1 mCi/ml; NEN). Supernatants were precleaned at 800×g for 30 min and centrifuged through a 20% sucrose cushion at 20,000 rpm (Beckman SW28 rotor) for 2 h to obtain virus pellets. Lysed cells, virus pellets, and supernatants without virus pellets were subjected to radioimmunoprecipitation analysis (RIPA) with HIV-1-positive human sera as previously described (Yu et al., J. Virol. 64:5688–5693, 1990). For immunoblot analysis of the virion proteins, virus pellets were prepared from the supernatants of COS-7 cells 72 h posttransfection as described above. Virion proteins were separated by sodium dodecyl sulfate-polyacrylamide gel electrophoresis and reacted with HIV-1-positive sera or sheep anti-gp120 serum. For the pulse-chase experiment, COS-7 cells (60 h posttransfection) were labeled in the RPMI 1640 media containing [³⁵S]cysteine for 30 min and then chased in the complete media for 0.5, 1.5, 3, and 6 h before being analyzed by RIP.

Construction of MA deletion mutants. The matrix protein of HIV-1 (MA) consists of 132 amino acids. Site-directed mutagenesis was applied to generate in-frame deletion mutants of MA, D1, D2, D4, D5, D7 and D8 contained deletions of 10 to 15 amino acids in MA (FIG. 1). D3 and D6 contained deletions of 9 and 10 amino acids, respectively, as well as substitutions of leucine to isoleucine at positions 41 and 78, respectively (FIG. 1).

IV. EXAMPLES

The following examples are provided to illustrate the invention not to limit it.

Example I

Mutations in MA which disrupt the incorporation of Env proteins.

A. The effect of MA mutations on Gag polyprotein synthesis, processing, and virus production. To analyze the efffect of MA mutations on virus assembly, mutant and wild-type proviral DNA were transfected into COS-7 cells by the DEAE-dextran method (Viglianti and Mullins, J. Virol. 62:4523–4532, 1988). Seventy-two hours posttransfection, virion-associated RT activity was measured by using supernatants from transfected cells. D4, D5, and D6 had a 2- to 10-fold decrease in virus production compared with production of the wild-type virus (FIG. 2). Virus production in the other MA mutants was approximately two- to five-fold greater than production of the wild-type virus as measured by RT activity in the supernatants of transfected cells (FIG. 2). Since mutations in D4, D5, and D6 significantly affected virus assembly, further studies focused on mutants D1, D2, D3, D7, and D8, unless otherwise indicated.

Sixty hours posttransfection, cells were metabolically labeled with ³⁵[S]cysteine for 12 h and analyzed by RIP. Similar levels of gp120 and gp160 were detected in wild-type and mutant-transfected cells, suggesting that the efficiencies of transfection were comparable (FIG. 3b). gp120 was also detected in the supernatants of wild-type and mutant-virus-transfected cells, implying that the transport of viral Env proteins was not affected by the MA mutations (FIG. 3a). The Gag precursor polyprotein, p55, and the processed products, p24/p25 and MA, were also detected in the wild-type-transfected cells (FIG. 3b). The level of p55 detected in some of the mutant-transfected cells was lower than that in the wild-type-transfected cells (FIG. 3b). The processing of the mutant Gag polyproteins was apparently not affected, as p24/p25 and mutant MA were detected in mutual-transfected cells (FIG. 3b) and/or virus pellets (FIG. 3c). Mutant MA was less detectable than wild-type MA in transfected cells (FIG. 3b), suggesting that it was either very unstable or less immunogenic than the wild-type MA.

The supernatants from the labeled COS-7 cells were used to purify released virions and subjected to RIPA. In wild-type virions, p24 and MA were detected (FIG. 3c). MA mutants D1, D2, D3, D7, and D8 produced more virions that the wild-type virus as determined by the increased level of p24, p34, and in some cases MA (D1 and D2) (FIG. 3c). Slightly smaller MA proteins, corresponding to detections in the 17 mutants, were detected in all of the mutant virions (FIG. 3c). The level of MA detected in the D3 and D7 virions was much lower than that of the wild-type MA (FIG. 3c). This may be due to the decreased immunogenicity of mutant MA. Then labeled virions were analyzed prior to immunoreaction, the ratios of MA to p24 in wild-type and D3 mutant virions were found to be the same (data not shown).

Figure 3D:
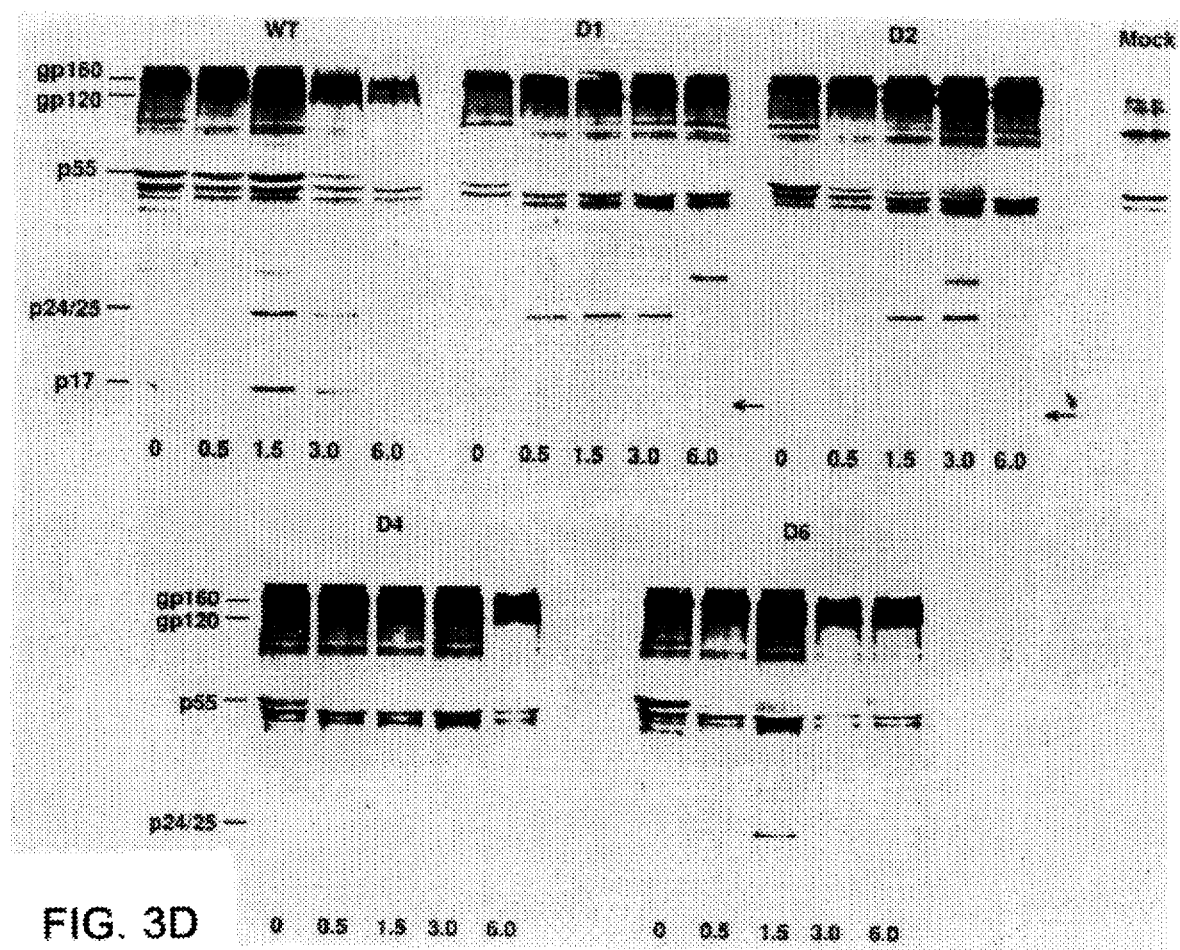

Viral protein synthesis and processing were also analyzed by pulse-chase experiments. The synthesis of mutant Gag p55 was not greatly affected as indicated by the pulse-labeling, whereas mutant p55 disappeared more quickly than wild-type p55 (FIG. 3d). This was observed both for mutants that had defects in virus assembly (D4 an D6) and for mutants that had slightly increased virus production (D1, D2, D3, D7, and D5) (FIG. 3d and data not shown).

Figure 5A:
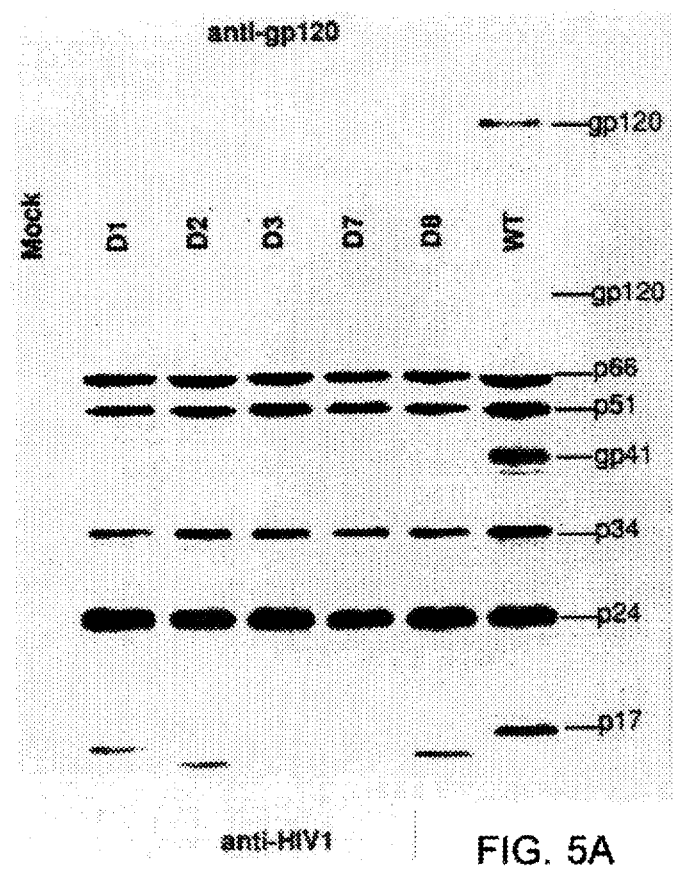

B. Mutation in MA affects viral Env protein incorporation into mature virions. To further analyze the defect of these MA mutants, virions were collected from the culture supernatants 72 h posttransfection. Comparable amounts of wild-type and mutant virions as adjusted by RT activity were used for an immunoblot assay. In the wild-type virions, Env proteins (gp41 and gp120), Gag proteins (p24 and MA), and Pol proteins) p66, p51, and p34) were detected (FIG. 5). The amounts of p24 and pol-encoded proteins p66, p51, and p34 detected in D1, D2, D3, D7, and D8 virions were comparable to these detected in the wild-type virions. In D1, D2, and D8, mutant MA was also detected (FIG. 5). Mutant MA was not detected in D3 and D7 virions, probably because of the loss of immunogenicity as described above. The most dramatic defect of the MA mutant virions was that the env-encoded proteins gp41 and gp120 were barely detectable in the virions of the MA mutants by using HIV-1-positive human sera (FIG. 5). Also, no gp120 was detected in MA mutant virions by using the sheep anti-gp120 serum (FIG. 5). Since the synthesis, processing, and transport of viral Env proteins seem unaffected in cells transfected by MA mutants (FIGS. 3a and b), these observations suggest that the viral Env proteins were not efficiently incorporated into the MA mutant virions.

Figure 6:
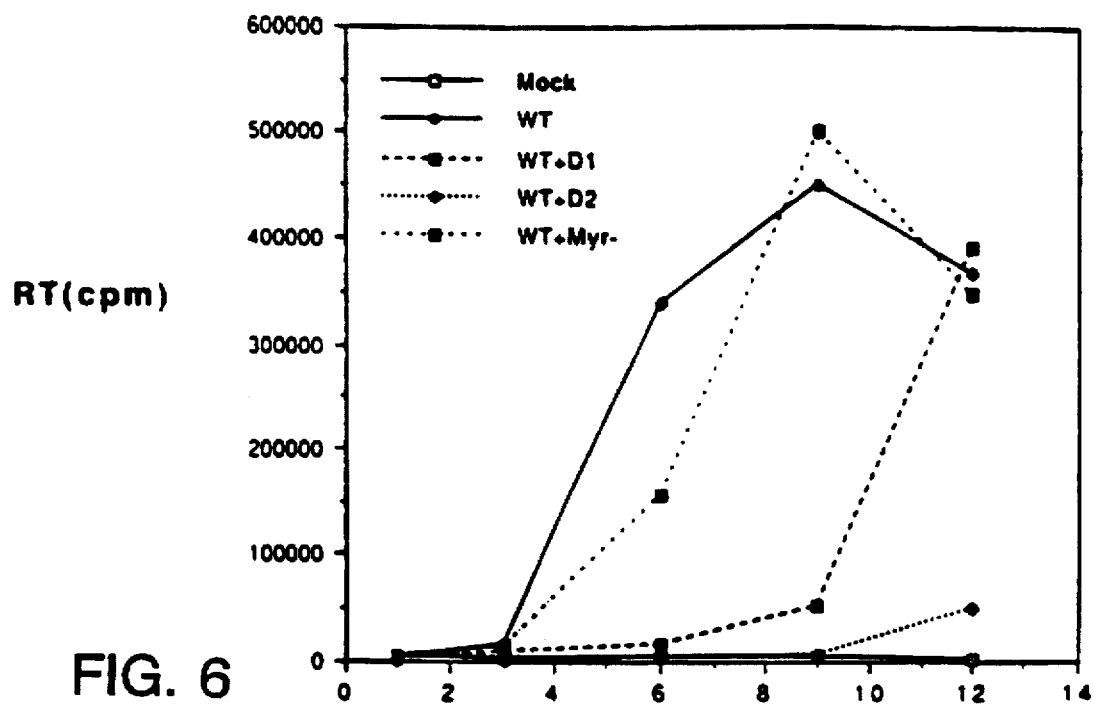

C. MA deletion mutants interfere the replication of wild-type virus. The deletion mutants described herein did not block virus assembly and release, suggesting that mutant Gag polyproteins can retain their ability to interact with each other and form particles. If the MA mutant Gag polyproteins can still interact with the wild-type Gag polyproteins and assemble into virions, the incorporation of Env proteins and infectivity of these resulting virions might be impaired. To test this possibility, wild-type DNA was cotransfected with either D1 or D2 DNA into SupT1 cells. Virus product,as mentioned by RT activity in the supernatants of transfected cells, was quicker and higher in cells transfected wild-type DNA alone than in cells cotransfected with wild-type and D1 or D2 DNAs (FIG. 6). Syncytium formation and cytopathic effects were also delayed in cells cotransfected with wild-type and D1 or D2 DNAs (data not shown). As a control, wild-type DNA was cotransfected with the myristylation mutant, Myr⁻, into SupT1 cells. Myristylation mutant Gag polyproteins of MuLV and spleen necrosis virus were unable to interact with the wild-type Gag polyproteins and were excluded from virus particles (Schultz and Rein, J. Virol. 63:2370–2373, 1989; Weaver and Panganiban, J. Virol. 64:3995–4001, 1990). If the myristoylation mutant Gag polyprotein of HIV-1 cannot interact with the wild-type Gag polyprotein, cotransfection of wild-type and Myr⁻ DNAs should not significantly interfere with the replication of wild-type virus. As expected, virus production (FIG. 6) and the cytopathic effect were not significantly affected in cells cotransfected with wild-type and Myr⁻ compared with cells transfected with wild-type alone.

D. Point mutations which prevent Env protein incorporation.

Figure 5B:
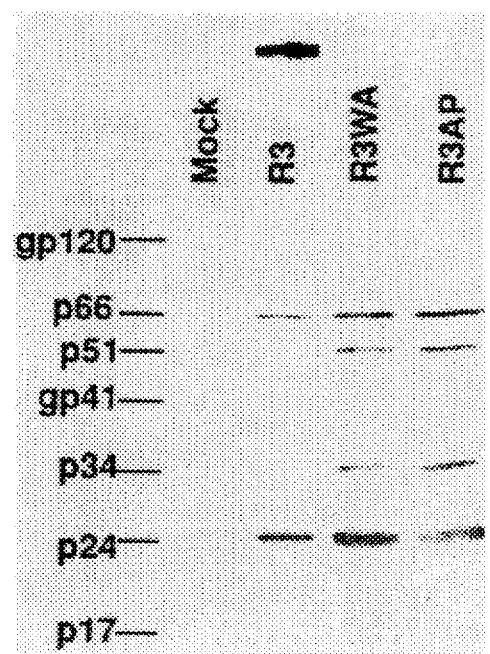

The incorporation of R2WA and R3AP Env mutant proteins into virions was compared with the incorporation of wild type proteins from virus R3 using immunoblot as described above. Although Gag proteins and Pol proteins were detected at comparable levels in mutant and wild type virions, the amount of Env proteins detected mutant virions was significantly decreased compared to that of wild type virions (FIG. 5B).

Example 2

Mutations in MA which disrupt virus entry into uninfected cells: MA mutations D9 and D10

A series of in-frame deletion mutations in the MA protein of human immunodeficiency virus type 1 (HIV-1) were generated. Two of these mutations did not affect virus assembly and were analyzed for their potential defects in the early steps of the virus life cycle.

Mutant D9 contains an in-frame deletion of 10 amino acids (105 through 114) and a substitution of isoleucine with leucine at position 104 at the carboxy terminus of p17 (FIG. 7A). Mutant D10 contains a deletion of 13 amino acids (116 through 128) at the carboxy terminus of p17 (FIG. 7A). Wild-type (wt) DNA (HXB2R3 Yu et al. (1992) J. Virol 66:4966–4971) and mutant DNA (D9 and D10) were transfected into COS-7 cells by the DEAE-dextrian method (Viglianti and Mullins, J. Virol. 62:4523–4532, 1988). Seventy-two hours posttransfection, comparable virion-associated reverse transcriptase (RT) activities were detected in the supernatants of cells transfected with wt and mutant DNAs (data not shown). This suggests that the assembly and release of virions were not significantly affected by the amino acid deletions introduced in D9 and D10. Cell-free wt and mutant viruses with comparable reverse transcriptase activities were tested on Sup-T1 cells for their infectivity. The infectivity of mutant viruses was significantly impaired compared with that of the wt virus. The production of mutant D9 virus was delayed by approximately 10 days, as monitored by RT activity in the supernatants of infected cells (FIG. 7C). Virus production was delayed even more dramatically in cells infected with mutant D10 (FIG. 7C), with no virus production detected in the first 30 days postinfection (FIG. 7C). Cytopathic effects and syncytium formation were also delayed in D9- and D10-infected Sup-T1 and H9 cells.

To determine whether mutations in D9 and D10 affect viral Gag protein synthesis, processing or assembly of viral proteins into mature virions, cell and viral lysates from transfected COS-7 cells were subjected to radioimmunoprecipitation assay and immunoblot analysis. COS-7 cells were metabolically labeled with [$^{35}$S]cysteine from 60 to 75 h posttransfection. Cell lysates were prepared and immunoprecipitated with HIV-1 positive human sera as previously described (Yu et al., J. Virol. 64:5688–5693, 1990). The Gag precursor (p55) and the partially cleaved Gag protein (p41), as well as the cleaved products, p24/p25 and p17, were detected in the wt cell lysate (FIG. 2A). Gag-related proteins P55, P41, P24/25, and P17 were also detected in D9 and D10 cell lysates (FIG. 7A). Mutant P55, P41, and P17 migrated more quickly than the wt Gag proteins, corresponding to the deletions in P17. It appears that the synthesis and processing of mutant Gag proteins were not greatly affected by deletions in D9 and D10.

Figure 8A:
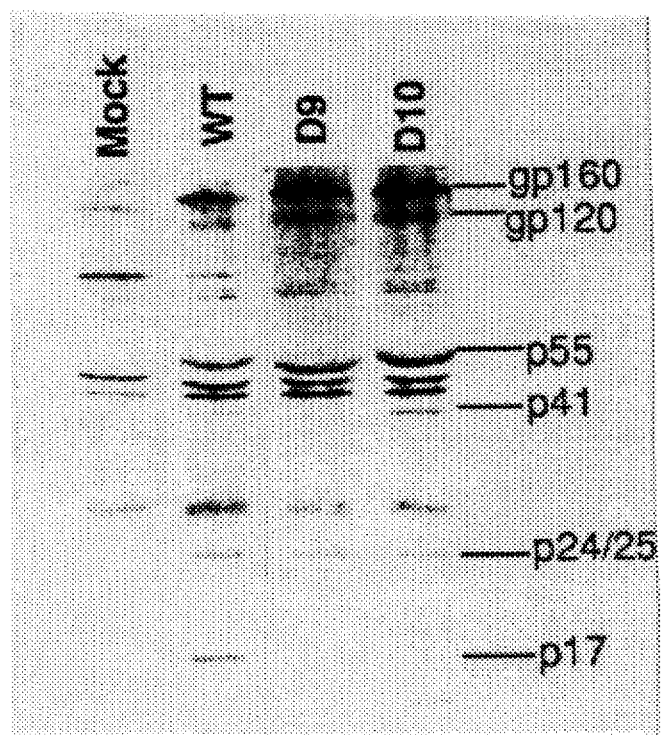
Figure 8B:
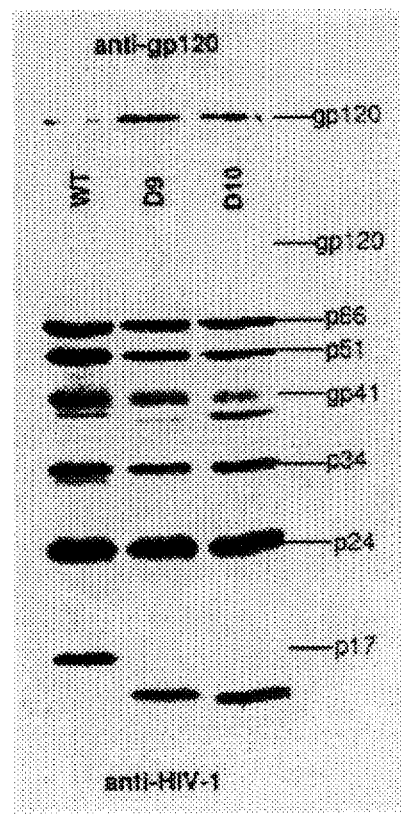
Figure 8C:
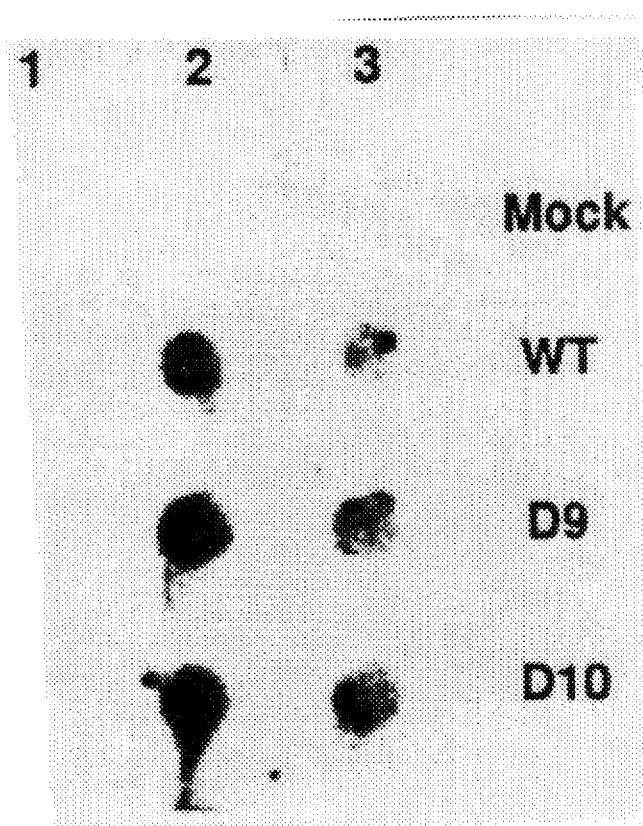

Viral proteins in mature virions were analyzed by immunoblot using viral pellets from the supernatants of transfected COS-7 cells. Gag proteins P24 and P17, Pol proteins p66, p51, and p34, and Env proteins gp 120 and gp41 were detected in wt and mutant virions by the HIV-1-positive sera (FIG. 8B). gp120 was also detected in wt and mutant virions by a sheep anti-gp120 serum (FIG. 8B). There was no significant difference between wt and mutant virions in either the amount or the migration of viral proteins, with the exception that the mutant p17s migrated faster than the wt p17 (FIG. 8B). These results suggest that deletions in D9 and D10 did not affect the cleavage of MA, CA, or Pol proteins in mature virions. The cleavage of NC protein from P15 was also not affected in mutant virions.

Figure 4:
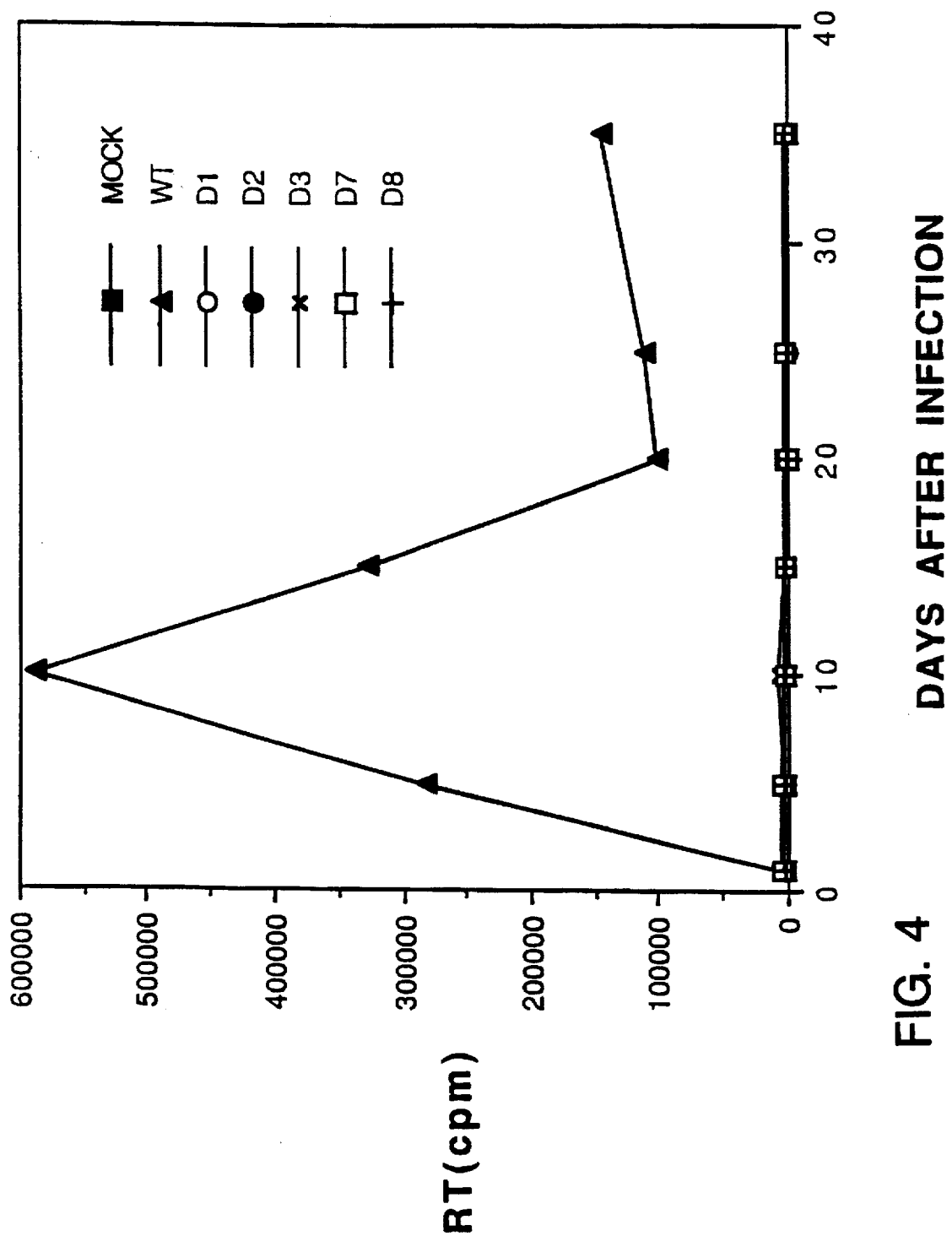
Figure 7C:
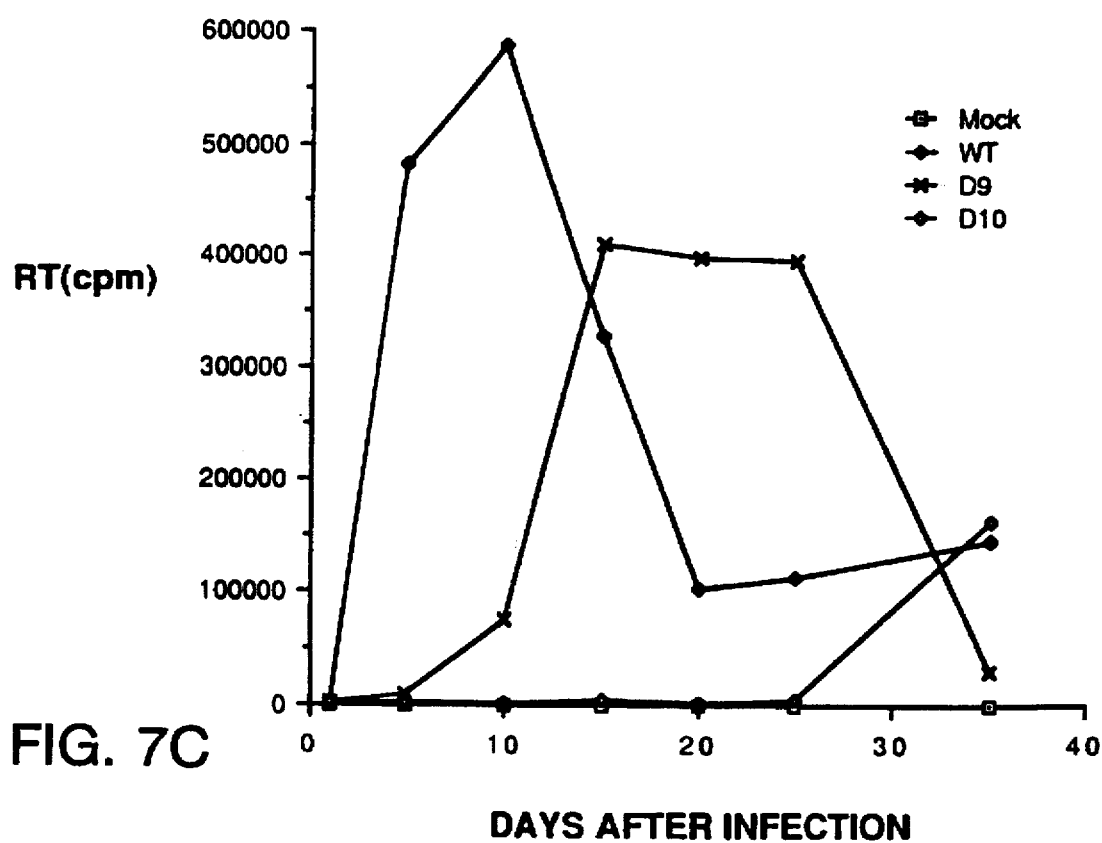
Figure 9:
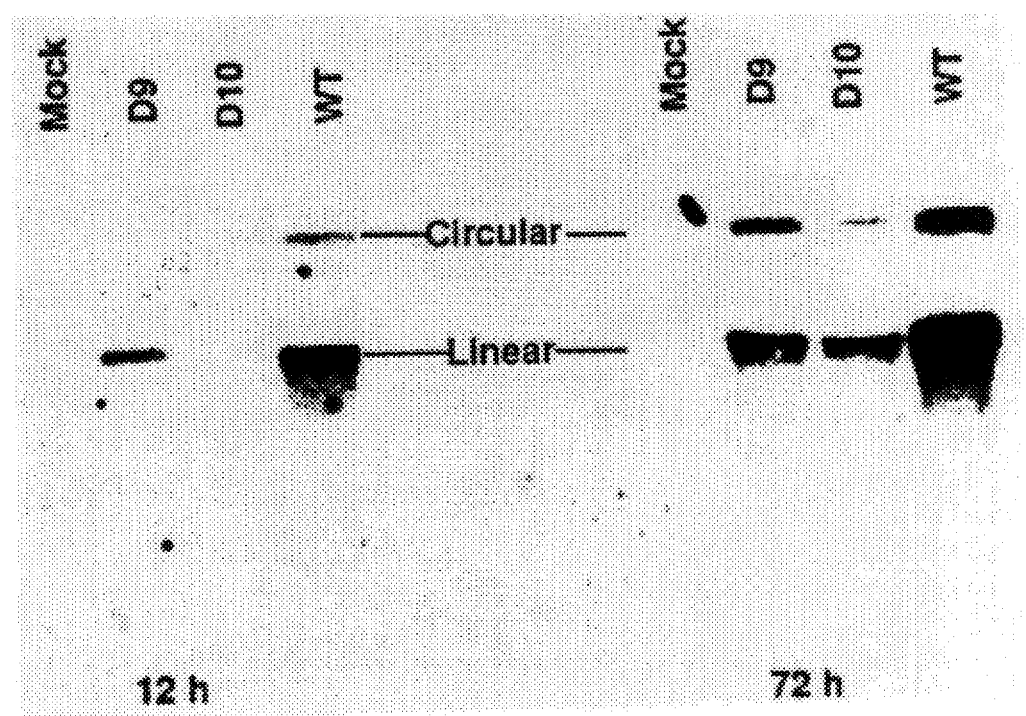

Deletions in D9 and D10 did not appear to affect the late steps of the virus life cycle, such as viral protein synthesis and processing and virus assembly and release. However, both mutant viruses had severe defects in virus infectivity, suggesting that early steps in the virus life cycle were affected. To test this possibility, the synthesis of the first viral product (viral DNA) was monitored immediately after infection. If the defect of the mutant viruses involved early steps in the virus life cycle, viral DNA synthesis would be blocked. Equal amounts of wt and mutant viruses from the supernatants of transfected COS-7 cells, as measured by virion-associated RT activity and viral proteins (FIG. 8B), were incubated with Sup-T1 cells at 37° C. for 2 h. Cells were then washed twice with phosphate-buffered saline and resuspended in fresh media. Twelve hours postinfection, viral DNAs were isolated from equal numbers of cells by the Hirt method (Hirt, J. Mol. Biol. 26:5707–5717, 1967) and analyzed by Southern blot (Southern, J. Mol. Biol. 98:503–517, 1975). A strong band migrating at the position of linear HIV-1 DNA (approximately 9.7 kb) was detected in the wt-infected cells (FIG. 9). A weaker band, which migrated more slowly than a 12-kb band would and which presumably was the circular form of HIV-1 DNA, was also detected in wt-infected cells (FIG. 9). Although it is possible that virions may carry some input plasmid DNA, the viral DNA isolated from infected cells by the method of Hirt is unlikely to be the input plasmid DNA. The signal of wt HIV-1 DNA was stronger at 72 h postinfection than at 12 h postinfection (FIG. 9), suggesting the presence of newly synthesized viral DNA. Also, under the same condition, the input plasmid DNA migrated differently from the viral DNA isolated by the method of Hirt. Both D9 and D10 viruses showed a significant decreased ability to synthesize viral DNA after infection (FIG. 4). The defect was more dramatic for D10 than for D9, corresponding to the results of the virus infectivity assay (FIG. 7C). Viral DNA synthesis at 72 h postinfection was also impaired in D9 - and D10-infected cells compared with that in cells infected with the wt virus (FIG. 9). This suggests that the spread of mutant viruses was also affected.

Deletions in D9 and D10 did not affect the synthesis and cleavage of HIV-1 Gag protein or the assembly and release of virions. Therefore, our study suggests that the MA protein itself plays a role in the early steps of the viral life cycle, such as virus penetration or uncoating.

Figure 10:
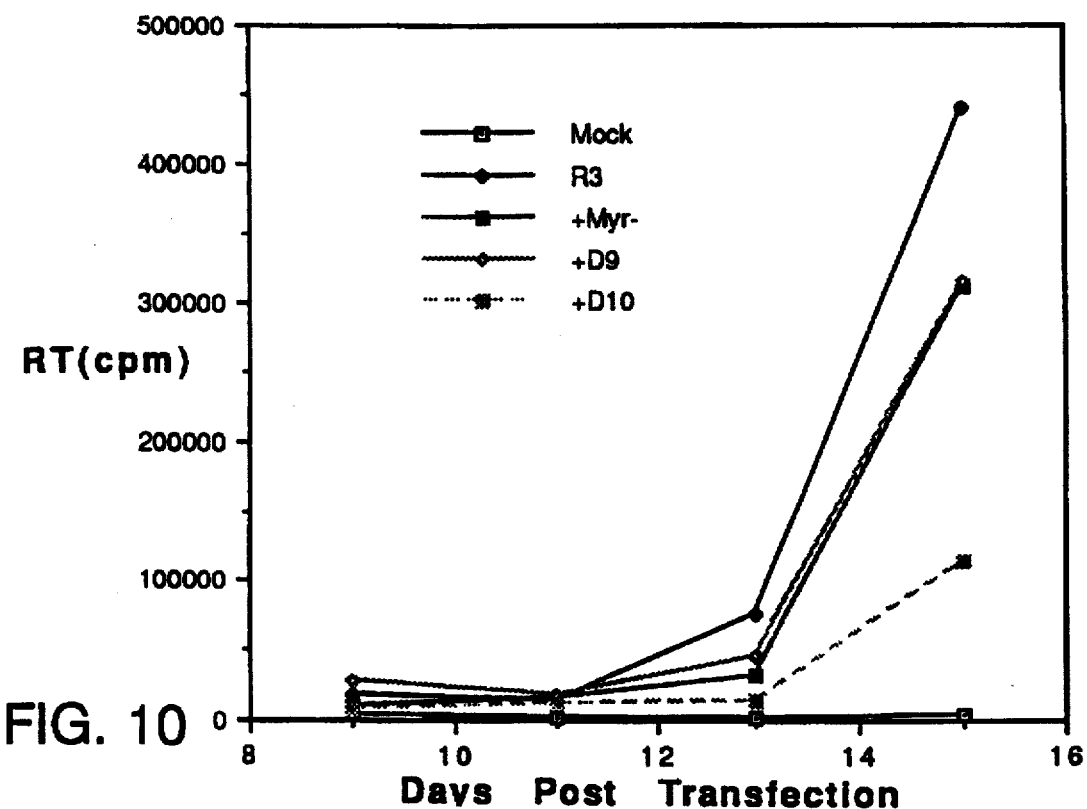

The effect of mutant D9 and D10 to interfere with wt virus replication was analyzed by cotransfection study as described in FIG. 6. The inhibitory effect of D9 appeared to be minimum as there was no significant difference in the curve of RT activity in wt cotransfected with D9 and control DNA Mry– (FIG. 10). In contrast, cotransfection of wt and D10 DNA resulted in significant reduction in virus production (FIG. 10).

Example 3

Mutations in MA which disrupt virus assembly and release.

Figure 12:
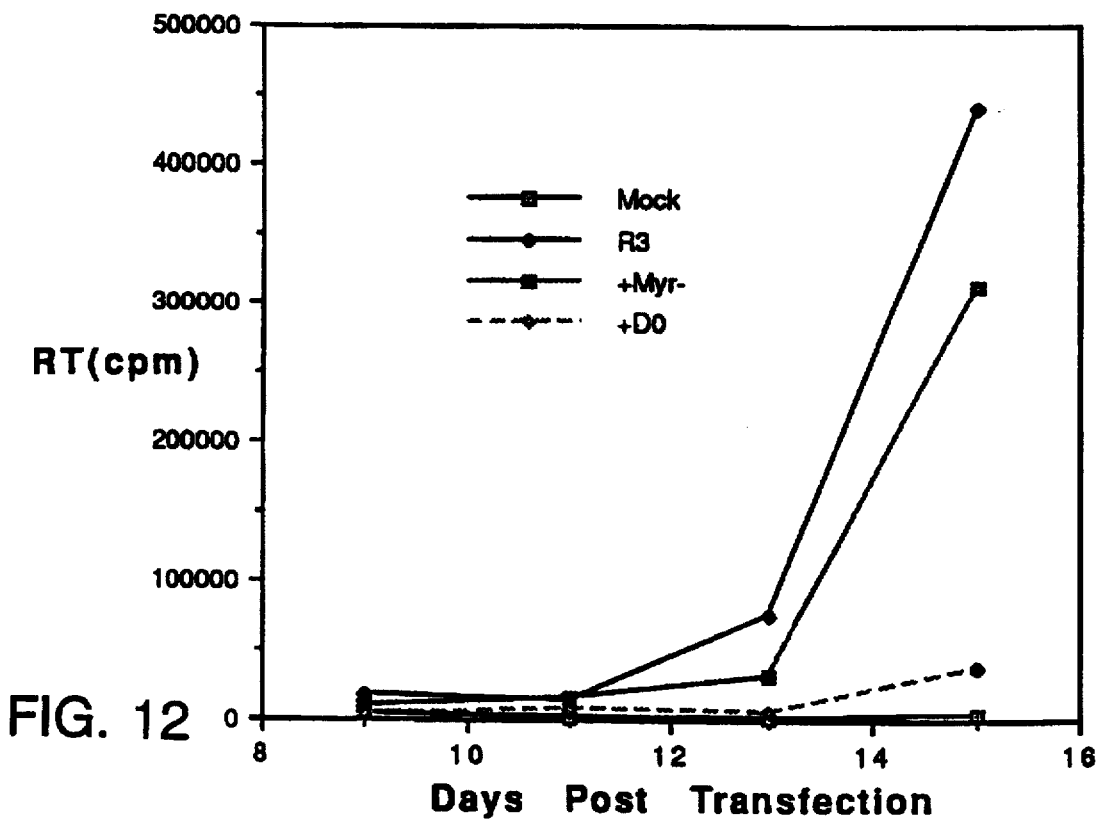
Figure 11A:
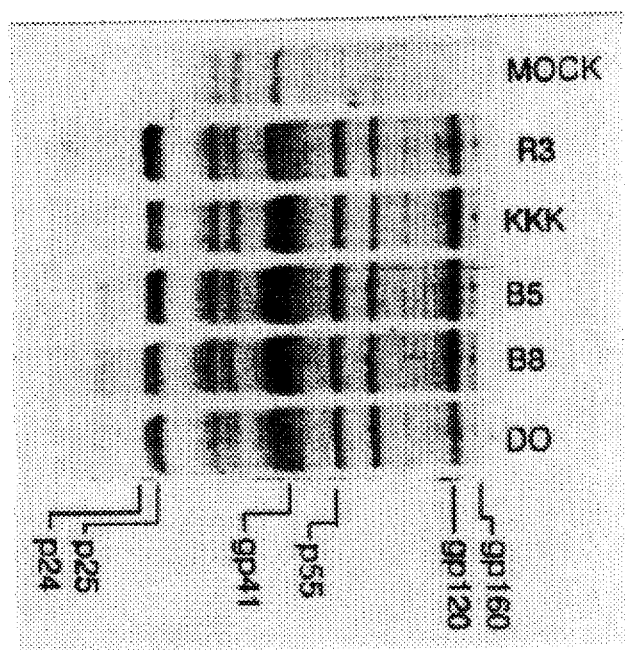
Figure 11B:
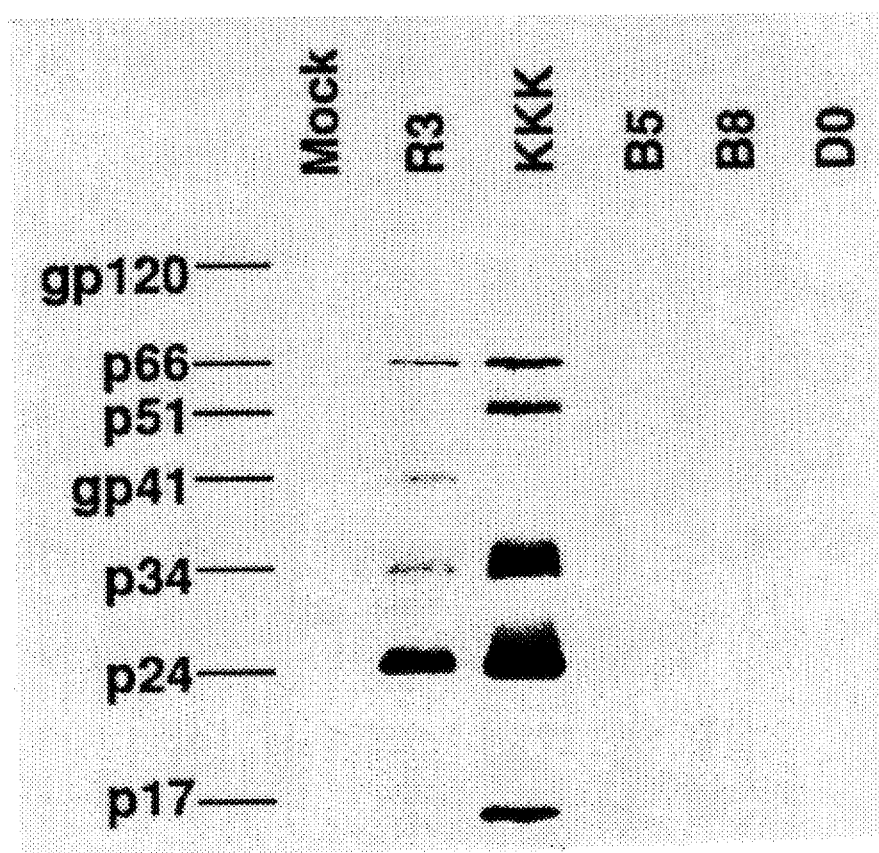
Figure 13:
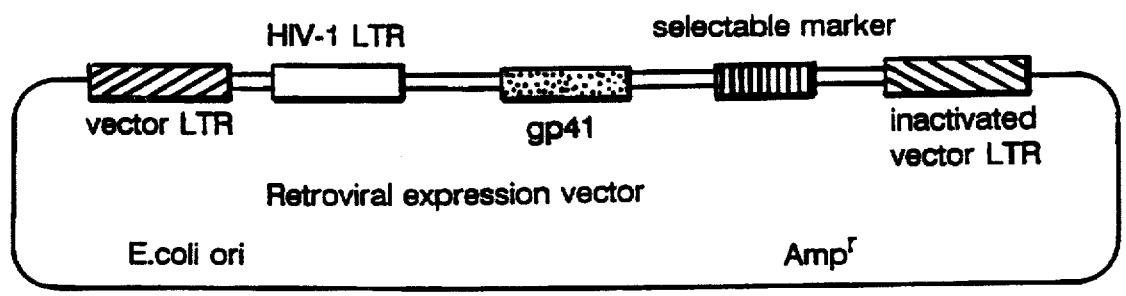

Mutations of HIV-1 MA coding region also affect virus assembly. Mutant D0 contains a deletion of amino acids 5 to 16 of the MA domain. Mutant B5 contains amino acid substitutions of Arg20 to Thr20, Lys26, 27, 28, and 32 to Glu26, 27, 28, and 32 respectively. Mutant B8 contains amino acid substitutions of Arg20 to Thr 20, Lys 18, 26, 27, 28, 30, and 32 to Asn18, 26, 27, 28, 30, and 32 respectively, and Arg20 and 22 to Gly20 and 22 respectively. Virus production of D0, B5, and B8 was compared to that of wt virus. Comparable amount of gp160, gp120, p55, and p24/25 was detected in wt, D0, B5, and B8 transfected COS-7 cells (FIG. 11). However, dramatic reduction in the amount of p24, p66, p51, and p34 was observed for mutant D0, B5, and B8 compared to that of the wt virus (FIG. 11). These results suggest that the assembly of these mutant virus are significantly affected. Cotransfection study indicated that D0 could significantly inhibit wt virus replication (FIG. 12).

Other Embodiments

MA Polypeptides

As described above, the invention includes therapies using any protein which is homologous to simian immunodeficiency virus/human immunodeficiency virus (SIV/HIV) MA (FIG. 1 (SEQ ID NO: 1) (SEQ ID NO: 2)) as well as other naturally occurring MA polypeptides. Also included are: allelic variations; natural mutants; induced mutants; proteins encoded by DNA that hybridizes under high (e.g., washing at 2×SSC at 40 C with a probe length of at least 40 nucleotides) stringency conditions to naturally occurring MA encoding nucleic acid (for other definitions of high and low stringency see Current Protocols in Molecular Biology, John Wiley & Sons, New York, 1989, 6.3.1–6.3.6, hereby incorporated by reference). The term also includes chimeric polypeptides that include MA together with unrelated sequences.

Figures 7A, 7B:
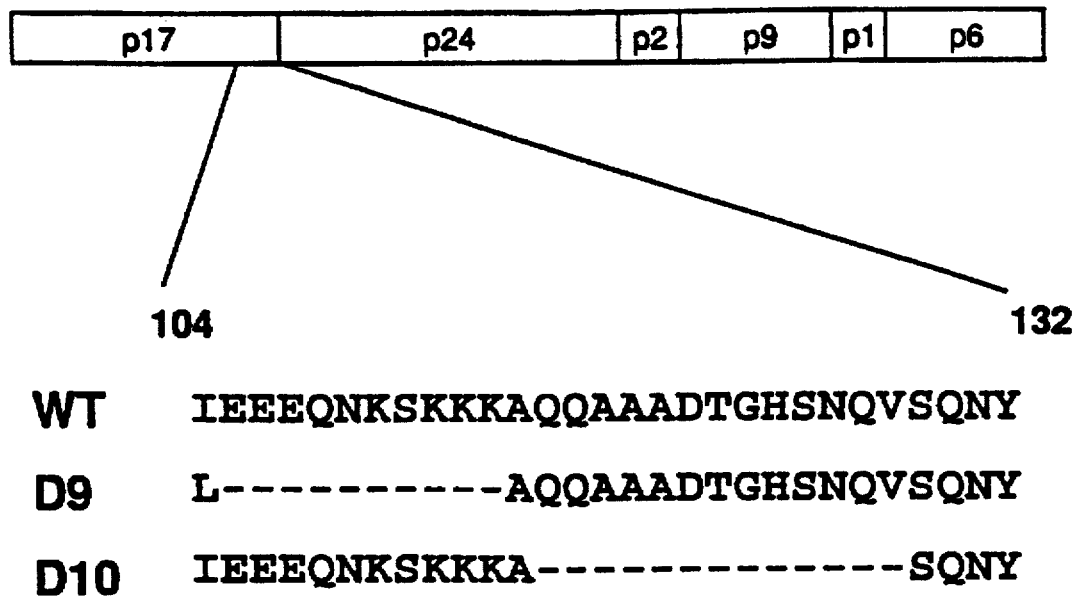

The invention also includes any biologically active fragment or analog of MA. By "biologically active" is meant possessing therapeutically useful anti-HIV activity which is characteristic of the MA polypeptides shown in FIGS. 1 and 5. Therapeutically useful activity of a MA fragment or MA analog, can be determined in any one (or more) of a variety of MA assays, for example, those assays described in this application. A MA analog possessing, most preferably 90%, preferably 40%, or at least 10% of the activity of MA polypeptides (shown in FIGS. 2 and 7), in any in vivo or in vitro MA assay (e.g., those described below), is considered biologically active and useful in the invention.

Preferred analogs include mutants whose sequences do not destroy the polypeptide's relevant anti-HIV biological activity as measured using in vivo or in vitro (e.g., those described above). Preferred analogs also include mutated MA (or biologically active fragments thereof) which are modified for the purpose of increasing peptide stability; such analogs may contain, for example, one or more desaturated peptide bonds or D-amino acids in the peptide sequence.

Analogs can differ from mutated MA by amino acid sequence differences or by modifications that do not affect sequence, or by both. Analogs of the invention will generally exhibit at least 65%, more preferably 80%, even more preferably 90%, and most preferably 95% or even 99%, homology with all or part of a mutated MA sequence. The length of comparison sequences will generally be at least about 15 amino acid residues, preferably more than 40 amino acid residues. Modifications include in vivo, or in vitro chemical derivatization of polypeptides, e.g., acetylation, glycosylation, or carboxylation. Also embraced are versions of the same primary amino acid sequence that have phosphorylated amino acid residues, e.g., phosphotyrosine, phosphoserine, or phosphothreonine. Analogs can differ from mutated MA by alterations of their primary sequence. These include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

In addition to substantially full-length polypeptides, the invention also includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of MA can be generated by methods known to those skilled in the art. The ability of a candidate fragment to exhibit a biological activity of MA can be assessed by methods described below. Also included are MA polypeptides containing amino acids that are normally removed during protein processing (if any), including additional amino acids that are not required for the biological activity of the polypeptide (if any), or including additional amino acids (if any) that result from alternative mRNA splicing or alternative protein processing events.

The invention also includes polypeptides (or nucleic acid either encoding polypeptides) which are homologous to the mutated MA protein or homologous to the gag gene and are useful for the treatment of individuals infected with HIV. Sequences which are considered to be homologous are those which are 70% homologous. Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

What is claimed is:

1. A DNA construct comprising nucleic acid encoding a mutated human immunodeficiency virus (HIV) matrix (MA) polypeptide capable of undergoing wild-type gag proteolytic processing, said polypeptide being effective in lowering the incorporation of env polypeptides in the viral particle; disrupting viral assembly; or disrupting viral entry into uninfected cells.

2. The construct of claim 1 comprising nucleic acid encoding said mutated MA polypeptide, said nucleic acid being in an expressible genetic construction capable of transforming cells.

3. The construct of claim 2 in which said nucleic acid is part of a viral vector capable of infecting isolated cells.

4. The construct of claim 1 in which said nucleic acid further comprises a sequence encoding a CD4-binding polypeptide.

5. The construct of claim 1 in which said nucleic acid further comprises a sequence encoding a gp120-binding polypeptide.

6. The construct of claim 3, wherein said viral vector is human immunodeficiency virus type I.

7. Nucleic acid encoding a mutated MA polypeptide, said mutated MA polypeptide containing a deletion of a region comprising at least one or more of amino acids 11 to 20 and said mutated MA polypeptide being effective to lower the incorporation of env polypeptides in the viral particle.

8. Nucleic acid encoding a mutated MA polypeptide, said mutated MA polypeptide containing a deletion of amino acids 21 to 31 of wild-type MA polypeptide, and said mutated MA polypeptide being effective to lower the incorporation of env polypeptides in the viral particle.

9. Nucleic acid encoding a mutated MA polypeptide, said mutated MA polypeptide containing a deletion of a region comprising at least one or more of amino acids 32 to 49, and said mutated MA polypeptide being effective to lower the incorporation of env polypeptides in the viral particle.

10. Nucleic acid encoding a mutated MA polypeptide, said mutated MA polypeptide containing a deletion of a region comprising at least one or more of amino acids 79 to 90, and said mutated MA polypeptide being effective to lower the incorporation of env polypeptides in the viral particle.

11. Nucleic acid encoding a mutated MA polypeptide, said mutated MA polypeptide containing a deletion of a region comprising at least one or more of amino acids 91 to 103, and said mutated MA polypeptide being effective to lower the incorporation of env polypeptides in the viral particle.

12. Nucleic acid encoding a mutated MA polypeptide, said mutated MA polypeptide containing a deletion of a region comprising at least one or more of amino acids 105 to 114, and said mutated MA polypeptide being effective to disrupt entry of viral particles into uninfected cells.

13. Nucleic acid encoding a mutated MA polypeptide, said mutated MA polypeptide containing a deletion of a region comprising at least one or more of amino acids 116 to 128, and said mutated MA polypeptide being effective to disrupt entry of viral particles into uninfected cells.

14. Nucleic acid encoding a mutated MA polypeptide, said mutated MA polypeptide containing a change of amino acids trp36 and ala37 to arg and pro, respectively, and said mutated MA polypeptide being effective to lower the incorporation of env polypeptides in the viral particle.

15. Nucleic acid encoding a mutated MA polypeptide, said mutated MA polypeptide containing a change of amino acid ala37 to pro, and said mutated MA polypeptide being effective to lower the incorporation of env polypeptides in the viral particle.

16. Nucleic acid encoding a mutated MA polypeptide, said mutated MA polypeptide containing a substitution of thr20 for arg20, and substitution of asn18, 26, 27, 28, 30 and 32 for lys18, 26, 27, 28, 30 and 32, and said mutated MA polypeptide being effective to disrupt viral assembly.

17. A nucleic acid construct encoding a mutated HIV matrix (MA) polypeptide, wherein said mutated MA polypeptide contains a deletion of at least one of the following regions of a wild type MA polypeptide:
   a) amino acids 5–16 of said wild-type;
   b) amino acids 11–20 of said wild-type;
   c) amino acids 21–31 of said wild-type;
   d) amino acids 32–49 of said wild-type;
   e) amino acids 79–90 of said wild-type;
   f) amino acids 91–103 of said wild-type;
   g) amino acids 105–114 of said wild-type;
   h) amino acids 116–128 of said wild-type.

18. A nucleic acid construct encoding a mutated HIV matrix (MA) polypeptide, wherein said mutated MA polypeptide contains at least one of the following substitutions of a wild type MA polypeptide:
   a) substitution of arg for trp36;
   b) substitution of pro for ala37;
   c) substitution of thr for arg20;
   d) substitution of glu for one or more of lys26, 27, 28, and 32;
   e) substitution of asn for one or more of lys18, 26, 27, 28, 30 and 32.

19. A nucleic acid construct according to claim 18 in which the substitution mutation is selected from the group consisting of:
   a) substitution of Arg for Trp36 and substitution of Pro for Ala37 (R3WA);
   b) substitution of Pro for Ala37 (R3AP);
   d) substitution of Thr for Arg20 and substitution of Glu for each of Lys26, 27, 28, and 32 (B5); and
   e) substitution of Thr for Arg20 and substitution of Asn for each of Lys18, 26, 27, 28, 30 and 32 (B8).

20. A nucleic acid construct according to claim 17, 18 or 19, said substitution being characterized in that said mutated MA polypeptide is effective for at least one of the following:
   (a) lowering the incorporation of Env polypeptides in the viral particle;
   (b) disrupting viral assembly; or
   (c) disrupting viral entry into uninfected cells.

21. A composition comprising cells containing nucleic acid encoding a mutated MA polypeptide, said nucleic acid being in an expressible genetic construction, wherein said mutated MA polypeptide is effective in lowering the incorporation of env polypeptides in the viral particle, disrupting viral assembly, or disrupting viral entry into uninfected cells.

22. The composition of claim 21 wherein said nucleic acid comprises a viral vector capable of infecting said cells.

23. The composition of claim 21 wherein said nucleic acid further comprises a sequence capable of encoding a CD4-binding polypeptide.

24. The composition of claim 21 wherein said nucleic acid further comprises a sequence encoding a gp120-binding polypeptide.

* * * * *

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 840
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
TCTCTGGCTA  ACTAGGGAAC  CCACTGCTTA  AGCCTCAATA  AAGCTTGCCT  TGAGTGCTTC   60

AAGTAGTGTG  TGCCCGTCTG  TTGTGTGACT  CTGGTAACTA  GAGATCCCTC  AGACCCTTTT  120

AGTCAGTGTG  GAAAATCTCT  AGCAGTGGCG  CCCGAACAGG  GACCTGAAAG  CGAAAGGGAA  180

ACCAGAGGAG  CTCTCTCGAC  GCAGGACTCG  GCTTGCTGAA  GCGCGCACGG  CAAGAGGCGA  240

GGGGCGGCGA  CTGGTGAGTA  CGCCAAAAAT  TTTGACTAGC  GGAGGCTAGA  AGGAGAGACA  300

TGGGTGCGAG  AGCGTCAGTA  TTAAGCGGGG  GAGAATTAGA  TCGATGGGAA  AAAATTCGGT  360

TAAGGCCAGG  GGGAAAGAAA  AAATATAAAT  TAAAACATAT  AGTATGGGCA  AGCAGGGAGC  420

TAGAACGATT  CGCAGTTAAT  CCTGGCCTGT  TAGAAACATC  AGAAGGCTGT  AGACAAATAC  480

TGGGACAGCT  ACAACCATCC  CTTCAGACAG  GATCAGAAGA  ACTTAGATCA  TTATATAATA  540

CAGTAGCAAC  CCTCTATTGT  GTGCATCAAA  GGATAGAGAT  AAAAGACACC  AAGGAAGCTT  600

TAGACAAGAT  AGAGGAAGAG  CAAAACAAAA  GTAAGAAAAA  AGCACAGCAA  GCAGCAGCTG  660

ACACAGGACA  CAGCAATCAG  GTCAGCCAAA  ATTACCCTAT  AGTGCAGAAC  ATCCAGGGGC  720

AAATGGTACA  TCAGGCCATA  TCACCTAGAA  CTTTAAATGC  ATGGGTAAAA  GTAGTAGAAG  780
```

AGAAGGCTTT CAGCCCAGAA GTGATACCCA TGTTTTCAGC ATTATCAGAA GGAGCCACCC    840

( 2 ) INFORMATION FOR SEQ ID NO: 2:

( i ) SEQUENCE CHARACTERISTICS:
        ( A ) LENGTH: 396
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
ATG  GGT  GCG  AGA  GCG  TCA  GTA  TTA  AGC  GGG  GGA  GAA  TTA  GAT  CGA  TGG     48
Met  Gly  Ala  Arg  Ala  Ser  Val  Leu  Ser  Gly  Gly  Glu  Leu  Asp  Arg  Trp
 1              5                        10                       15

GAA  AAA  ATT  CGG  TTA  AGG  CCA  GGG  GGA  AAG  AAA  AAA  TAT  AAA  TTA  AAA     96
Glu  Lys  Ile  Arg  Leu  Arg  Pro  Gly  Gly  Lys  Lys  Lys  Tyr  Lys  Leu  Lys
                20                        25                       30

CAT  ATA  GTA  TGG  GCA  AGC  AGG  GAG  CTA  GAA  CGA  TTC  GCA  GTT  AAT  CCT    144
His  Ile  Val  Trp  Ala  Ser  Arg  Glu  Leu  Glu  Arg  Phe  Ala  Val  Asn  Pro
           35                        40                       45

GGC  CTG  TTA  GAA  ACA  TCA  GAA  GGC  TGT  AGA  CAA  ATA  CTG  GGA  CAG  CTA    192
Gly  Leu  Leu  Glu  Thr  Ser  Glu  Gly  Cys  Arg  Gln  Ile  Leu  Gly  Gln  Leu
 50                       55                       60

CAA  CCA  TCC  CTT  CAG  ACA  GGA  TCA  GAA  GAA  CTT  AGA  TCA  TTA  TAT  AAT    240
Gln  Pro  Ser  Leu  Gln  Thr  Gly  Ser  Glu  Glu  Leu  Arg  Ser  Leu  Tyr  Asn
 65                       70                       75                      80

ACA  GTA  GCA  ACC  CTC  TAT  TGT  GTG  CAT  CAA  AGG  ATA  GAG  ATA  AAA  GAC    288
Thr  Val  Ala  Thr  Leu  Tyr  Cys  Val  His  Gln  Arg  Ile  Glu  Ile  Lys  Asp
                85                       90                       95

ACC  AAG  GAA  GCT  TTA  GAC  AAG  ATA  GAG  GAA  GAG  CAA  AAC  AAA  AGT  AAG    336
Thr  Lys  Glu  Ala  Leu  Asp  Lys  Ile  Glu  Glu  Glu  Gln  Asn  Lys  Ser  Lys
               100                      105                      110

AAA  AAA  GCA  CAG  CAA  GCA  GCA  GCT  GAC  ACA  GGA  CAC  AGC  AAT  CAG  GTC    384
Lys  Lys  Ala  Gln  Gln  Ala  Ala  Ala  Asp  Thr  Gly  His  Ser  Asn  Gln  Val
               115                      120                      125

AGC  CAA  AAT  TAC                                                                 396
Ser  Gln  Asn  Tyr
               130
```

( 2 ) INFORMATION FOR SEQ ID NO: 3:

( i ) SEQUENCE CHARACTERISTICS:
        ( A ) LENGTH: 13
        ( B ) TYPE: amino acid
        ( C ) STRANDEDNESS: Not Relevant
        ( D ) TOPOLOGY: linear ( x i ) SEQUENCE DESCRIPTION: SEQ ID NO: 3:

```
Ala  Asp  Thr  Gly  His  Ser  Asn  Gln  Val  Ser  Gln  Asn  Tyr
 1                    5                        10
```

( 2 ) INFORMATION FOR SEQ ID NO: 4:

( i ) SEQUENCE CHARACTERISTICS:
        ( A ) LENGTH: 10
        ( B ) TYPE: amino acid
        ( C ) STRANDEDNESS: Not Relevant
        ( D ) TOPOLOGY: linear ( x i ) SEQUENCE DESCRIPTION: SEQ ID NO: 4:

```
Gly  His  Ser  Asn  Gln  Val  Ser  Gln  Asn  Tyr
 1                    5                        10
```

( 2 ) INFORMATION FOR SEQ ID NO: 5:

(i) SEQUENCE CHARACTERISTICS:
 (A) LENGTH: 16
 (B) TYPE: amino acid
 (C) STRANDEDNESS: Not Relevant
 (D) TOPOLOGY: linear (xi) SEQUENCE DESCRIPTION: SEQ ID NO: 5:

Ile Glu Glu Glu Gln Asn Lys Ser Lys Lys Lys Ala Ser Gln Asn Tyr
1               5                   10                  15

(2) INFORMATION FOR SEQ ID NO: 6:

(i) SEQUENCE CHARACTERISTICS:
  (A) LENGTH: 10
  (B) TYPE: amino acid
  (C) STRANDEDNESS: Not Relevant
  (D) TOPOLOGY: linear (xi) SEQUENCE DESCRIPTION: SEQ ID NO: 6:

Ala Ala Asp Thr Gly His Ser Asn Gln Val
1               5                   10

(2) INFORMATION FOR SEQ ID NO: 7:

(i) SEQUENCE CHARACTERISTICS:
  (A) LENGTH: 10
  (B) TYPE: amino acid
  (C) STRANDEDNESS: Not Relevant
  (D) TOPOLOGY: linear (xi) SEQUENCE DESCRIPTION: SEQ ID NO: 7:

Ala Ala Glu Thr Gly His Thr Ser Gln Val
1               5                   10

(2) INFORMATION FOR SEQ ID NO: 8:

(i) SEQUENCE CHARACTERISTICS:
  (A) LENGTH: 10
  (B) TYPE: amino acid
  (C) STRANDEDNESS: Not Relevant
  (D) TOPOLOGY: linear (xi) SEQUENCE DESCRIPTION: SEQ ID NO: 8:

Ala Ala Glu Thr Gly His Thr Ser Asn Val
1               5                   10

(2) INFORMATION FOR SEQ ID NO: 9:

(i) SEQUENCE CHARACTERISTICS:
  (A) LENGTH: 10
  (B) TYPE: amino acid
  (C) STRANDEDNESS: Not Relevant
  (D) TOPOLOGY: linear (xi) SEQUENCE DESCRIPTION: SEQ ID NO: 9:

Ala Val Glu Thr Gly Ala Thr Asn Pro Leu
1               5                   10

(2) INFORMATION FOR SEQ ID NO: 10:

(i) SEQUENCE CHARACTERISTICS:
  (A) LENGTH: 10
  (B) TYPE: amino acid
  (C) STRANDEDNESS: Not Relevant
  (D) TOPOLOGY: linear (xi) SEQUENCE DESCRIPTION: SEQ ID NO: 10:

Ile Ala Glu Thr Gln His Gly Thr Ile Val ( 2 ) INFORMATION FOR SEQ ID NO: 11:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CCC CCT GGC CTT AAC CCG CTT AAT ACT        27

( 2 ) INFORMATION FOR SEQ ID NO: 12:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 12:

CCA TAC TAT ATG TTT TCG AAT TTT TTC CCA TCG        33

( 2 ) INFORMATION FOR SEQ ID NO: 13:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 13:

AAC TGC GAA TCG TTC TAT TAA TTT ATA TTT TTC        33

( 2 ) INFORMATION FOR SEQ ID NO: 14:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 14:

CAG TAT TTG TCT ACA GAG CTC CCT GCT TGC CC        32

( 2 ) INFORMATION FOR SEQ ID NO: 15:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 15:

TGA TCC TGT CTG AAG GCC TTC TGA TGT TTC        30

( 2 ) INFORMATION FOR SEQ ID NO: 16:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 16:

TAC TGT ATT ATA TAT CGA TGG TTG TAG CTG TCC        33

-continued ( 2 ) INFORMATION FOR SEQ ID NO: 17:

( i ) SEQUENCE CHARACTERISTICS:
( A ) LENGTH: 30
( B ) TYPE: nucleic acid
( C ) STRANDEDNESS: single
( D ) TOPOLOGY: linear ( x i ) SEQUENCE DESCRIPTION: SEQ ID NO: 17:

CTT TTA TCT CTA TTC TAG ATC TAA GTT CTT 30

( 2 ) INFORMATION FOR SEQ ID NO: 18:

( i ) SEQUENCE CHARACTERISTICS:
( A ) LENGTH: 30
( B ) TYPE: nucleic acid
( C ) STRANDEDNESS: single
( D ) TOPOLOGY: linear ( x i ) SEQUENCE DESCRIPTION: SEQ ID NO: 18:

TTG CTC TTC CTC TAT TTG ATG CAC ACA ATA 30

( 2 ) INFORMATION FOR SEQ ID NO: 19:

( i ) SEQUENCE CHARACTERISTICS:
( A ) LENGTH: 26
( B ) TYPE: nucleic acid
( C ) STRANDEDNESS: single
( D ) TOPOLOGY: linear ( x i ) SEQUENCE DESCRIPTION: SEQ ID NO: 19:

TGA CGC TCT CGC GAC CAT CTC TCT CC 26